(12) United States Patent
Gelfand et al.

(10) Patent No.: US 10,207,110 B1
(45) Date of Patent: Feb. 19, 2019

(54) DEVICES AND METHODS FOR TREATMENT OF HEART FAILURE VIA ELECTRICAL MODULATION OF A SPLANCHNIC NERVE

(71) Applicants: Mark Gelfand, New York, NY (US); Tamara Colette Baynham, Bowie, MD (US); Howard Levin, Teaneck, NJ (US)

(72) Inventors: Mark Gelfand, New York, NY (US); Tamara Colette Baynham, Bowie, MD (US); Howard Levin, Teaneck, NJ (US)

(73) Assignee: Axon Therapies, Inc., New York, NY (US)

( * ) Notice: Subject to any disclaimer, the term of this patent is extended or adjusted under 35 U.S.C. 154(b) by 0 days.

(21) Appl. No.: 15/293,021

(22) Filed: Oct. 13, 2016

Related U.S. Application Data

(60) Provisional application No. 62/240,864, filed on Oct. 13, 2015.

(51) Int. Cl.
*A61N 1/36* (2006.01)
*A61N 1/05* (2006.01)
*A61B 5/00* (2006.01)
*A61N 1/362* (2006.01)

(52) U.S. Cl.
CPC ........ *A61N 1/36114* (2013.01); *A61B 5/4848* (2013.01); *A61N 1/0556* (2013.01); *A61N 1/3627* (2013.01); *A61N 1/36135* (2013.01)

(58) Field of Classification Search
CPC .............. A61N 1/0556; A61N 1/36057; A61N 1/3606; A61N 1/36114; A61N 1/362
See application file for complete search history.

(56) References Cited

U.S. PATENT DOCUMENTS

| | | |
|---|---|---|
| 3,301,258 A | 1/1967 | Werner |
| 5,447,529 A | 9/1995 | Marchlinski et al. |
| 5,454,840 A | 10/1995 | Krakovsky et al. |
| 5,458,626 A | 10/1995 | Krause |
| 6,044,846 A | 4/2000 | Edwards |
| 6,058,331 A | 5/2000 | King |
| 6,165,172 A | 12/2000 | Farley et al. |
| 6,236,886 B1 | 5/2001 | Cherepenin et al. |
| 6,569,160 B1 | 5/2003 | Goldin et al. |
| 6,658,929 B2 | 12/2003 | Atkinson |
| 6,760,616 B2 | 7/2004 | Hoey et al. |
| 6,832,114 B1 | 12/2004 | Whitehurst et al. |

(Continued)

FOREIGN PATENT DOCUMENTS

| | | |
|---|---|---|
| WO | WO2016/084081 A2 | 6/2016 |
| WO | WO2016/176333 A1 | 11/2016 |

(Continued)

OTHER PUBLICATIONS

Brooksby et al.; Dynamic changes in splanchnic blood flow and blood volume in dogs during activation of sympathetic nerves; Circulation Research; XXIX(3); pp. 227-238; Sep. 1971.

(Continued)

*Primary Examiner* — Allen Porter, Jr.
(74) *Attorney, Agent, or Firm* — Shay Glenn LLP

(57) ABSTRACT

Disclosed herein is a device, and method for treating heart failure by electrically modulating a splanchnic nerve with an implantable device.

12 Claims, 18 Drawing Sheets

(56) References Cited

U.S. PATENT DOCUMENTS

| | | | |
|---|---|---|---|
| 6,849,073 B2 | 2/2005 | Hoey et al. | |
| 6,885,888 B2 | 4/2005 | Rezai | |
| 6,890,315 B1 | 5/2005 | Levin et al. | |
| 7,054,689 B1 | 5/2006 | Whitehurst et al. | |
| 7,149,574 B2 | 12/2006 | Yun et al. | |
| 7,236,822 B2 | 6/2007 | Dobak, III | |
| 7,239,912 B2 | 7/2007 | Dobak, III | |
| 7,282,050 B2 | 10/2007 | Starkebaum et al. | |
| 7,330,762 B2 | 2/2008 | Boveja et al. | |
| 7,367,972 B2 | 5/2008 | Francischelli et al. | |
| 7,418,292 B2 | 8/2008 | Shafer | |
| 7,427,280 B2 | 9/2008 | Gerber | |
| 7,529,582 B1 | 5/2009 | DiLorenzo | |
| 7,532,938 B2 | 5/2009 | Machado et al. | |
| 7,551,964 B2 | 6/2009 | Dobak, III | |
| 7,599,736 B2 | 10/2009 | DiLorenzo | |
| 7,623,924 B2 | 11/2009 | Narciso, Jr. | |
| 7,689,276 B2 | 3/2010 | Dobak | |
| 7,689,277 B2 | 3/2010 | Dobak, III | |
| 7,702,386 B2 | 4/2010 | Dobak et al. | |
| 7,769,442 B2 | 8/2010 | Shafer | |
| 7,778,703 B2 | 8/2010 | Gross et al. | |
| 7,860,570 B2 * | 12/2010 | Whitehurst | A61N 1/37205 607/118 |
| 7,865,237 B2 | 1/2011 | Machado et al. | |
| 7,877,146 B2 | 1/2011 | Rezai et al. | |
| 7,937,145 B2 | 5/2011 | Dobak | |
| 8,007,496 B2 | 8/2011 | Rioux et al. | |
| 8,155,744 B2 | 4/2012 | Rezai | |
| 8,241,273 B2 | 8/2012 | Whayne et al. | |
| 8,270,568 B2 | 9/2012 | Pitt | |
| 8,295,926 B2 | 10/2012 | Dobak, III | |
| 8,321,030 B2 | 11/2012 | Maniak et al. | |
| 8,399,443 B2 | 3/2013 | Seward | |
| 8,401,667 B2 | 3/2013 | Gustus et al. | |
| 8,414,508 B2 | 4/2013 | Thapliyal et al. | |
| 8,433,412 B1 | 4/2013 | Westlund et al. | |
| 8,483,835 B2 | 7/2013 | Errico et al. | |
| 8,611,496 B2 | 12/2013 | Terunuma et al. | |
| 8,676,326 B1 | 3/2014 | Farazi | |
| 8,676,362 B2 | 3/2014 | Gabel et al. | |
| 8,798,738 B2 | 8/2014 | Machado et al. | |
| 8,814,793 B2 | 8/2014 | Brabrand | |
| 8,911,439 B2 | 12/2014 | Mayse et al. | |
| 8,994,536 B2 | 3/2015 | Margon | |
| 8,998,894 B2 | 4/2015 | Mauch et al. | |
| 9,005,100 B2 | 4/2015 | Gnanashanmugam et al. | |
| 9,022,948 B2 | 5/2015 | Wang | |
| 9,033,969 B2 | 5/2015 | Azamian et al. | |
| 9,162,075 B2 | 10/2015 | Sluijter et al. | |
| 9,199,091 B2 | 12/2015 | Danek et al. | |
| 9,345,530 B2 | 5/2016 | Ballakur et al. | |
| 9,345,900 B2 | 5/2016 | Wu et al. | |
| 9,370,657 B2 | 6/2016 | Tehrani et al. | |
| 9,439,580 B2 | 9/2016 | Hatlestad et al. | |
| 9,439,598 B2 | 9/2016 | Shimada et al. | |
| 9,743,845 B2 | 8/2017 | Wang | |
| 9,895,539 B1 | 2/2018 | Heit et al. | |
| 2003/0216792 A1 | 11/2003 | Levin et al. | |
| 2007/0167984 A1 | 7/2007 | Kieval et al. | |
| 2009/0036794 A1 | 2/2009 | Stubhaug et al. | |
| 2010/0168820 A1 * | 7/2010 | Maniak | A61N 1/36007 607/63 |
| 2010/0241113 A1 | 9/2010 | Ingle | |
| 2010/0305664 A1 | 12/2010 | Wingeier et al. | |
| 2011/0022127 A1 * | 1/2011 | Averina | A61B 5/0537 607/62 |
| 2011/0028962 A1 | 2/2011 | Werneth et al. | |
| 2011/0224750 A1 * | 9/2011 | Scheiner | A61N 1/36114 607/17 |
| 2011/0238083 A1 * | 9/2011 | Moll | A61B 8/12 606/130 |
| 2012/0089047 A1 | 4/2012 | Ryba et al. | |
| 2012/0265198 A1 | 10/2012 | Crow et al. | |
| 2012/0296329 A1 | 11/2012 | Ng | |
| 2013/0035682 A1 | 2/2013 | Weil | |
| 2013/0103026 A1 | 4/2013 | Kleshinski et al. | |
| 2013/0226201 A1 | 8/2013 | Miller et al. | |
| 2013/0237948 A1 | 9/2013 | Donders et al. | |
| 2013/0282000 A1 | 10/2013 | Parsonage et al. | |
| 2013/0296646 A1 | 11/2013 | Barbut et al. | |
| 2013/0331813 A1 | 12/2013 | Barbut et al. | |
| 2014/0058294 A1 | 2/2014 | Gross et al. | |
| 2014/0058377 A1 | 2/2014 | Deem et al. | |
| 2014/0067003 A1 | 3/2014 | Vase et al. | |
| 2014/0088585 A1 | 3/2014 | Hill et al. | |
| 2014/0088588 A1 | 3/2014 | Jarrard | |
| 2014/0214129 A1 | 7/2014 | Waataja et al. | |
| 2014/0276742 A1 | 9/2014 | Nabutovsky et al. | |
| 2014/0303617 A1 | 10/2014 | Shimada | |
| 2015/0141810 A1 | 5/2015 | Weadock | |
| 2015/0141985 A1 | 5/2015 | Mayse et al. | |
| 2015/0208949 A1 | 7/2015 | Tupin et al. | |
| 2015/0245867 A1 | 9/2015 | Gross | |
| 2015/0335286 A1 | 11/2015 | Boydell | |
| 2016/0158554 A1 | 6/2016 | Graig | |
| 2016/0163062 A1 | 6/2016 | Garber | |
| 2016/0192981 A1 | 7/2016 | Dimmer et al. | |
| 2016/0220851 A1 | 8/2016 | Mayse et al. | |
| 2016/0296171 A1 | 10/2016 | Drori et al. | |
| 2017/0049989 A1 | 2/2017 | Kapural | |
| 2017/0202614 A1 | 7/2017 | Gross et al. | |
| 2017/0216602 A1 * | 8/2017 | Waataja | A61N 1/36007 |

FOREIGN PATENT DOCUMENTS

| | | | |
|---|---|---|---|
| WO | WO2017/096007 A1 | 6/2017 | |
| WO | WO2017/197625 A1 | 11/2017 | |
| WO | WO2018/023132 A1 | 2/2018 | |

OTHER PUBLICATIONS

Burkhoff et al.; Why does pulmonary venous pressure rise after on of LV dysfunction: a theoretical analysis; Am. J. Physiol.; 265(5, pt. 2); pp. H1819-H1828; Nov. 1993.

Cody et al.; Captopril kinetics in chronic congestive heart failure; Clin pharmacol Ther.; 32(6); pp. 721-726; Dec. 1982.

Edwards Lifesciences; ClearSight System (brochure; No. AR11578); 4 pgs.; © 2014.

Fallick et al.; Sympathetically mediated changes in capacitance: Redistribution of the venous reservoir as a cause of decompensation; Circulation: Heart Failure; 4; pp. 669-675; Sep. 2011.

Fiaccadori et al.; Ultrafiltration in Heart Failure; Am Heart J.; 161(3); pp. 439-449; Mar. 2011.

Fujita; Splanchnic circulation following coeliac plexus block; Acta Anaesthesiol Scand.; 32(4); pp. 323-327; May 1988.

GAMBRO®; Aquadex FlexFlowTM (brochure, No. L5189 Rev. B); 4 pgs.; © Aug. 2011

Greenway; Blockade of reflex venous capacitance responses in liver and spleen by hexamethonium, atropine, and surgical section; Can. J. Physiol. Pharmacol.; 69(9); 1284-1287; Sep. 1991.

Kimura et al.; Application of electrical impedance analysis for diagnosis of a pulmonary mass; Chest; 105(6); pp. 1679-1682; Jun. 1994.

Nath et al.; Biophysics and pathology of catheter energy delivery systems; Progress in Cardiovascular Diseases; XXXVII(4); pp. 185-204; Jan./Feb. 1995.

Wroclaw Medical Univ. (Poland); Removing a section of nerve visceral improved (press release; with machine translation); retrieved Oct. 10, 2016 from the internet: http://www.zdrowie.abc.com.pl/aktualnosci/wroclaw-usuniecie-fragmentu-nerwu-trzewnege-poprawilo-u-chorej-wydolnosc-serca,25247.html; 5 pgs.; Sep. 23, 2016.

Levin et al.; U.S. Appl. No. 15/017,351 entitled "Devices and Methods for Treatment of Heart Failure by Splanchnic Nerve Ablation," filed Feb. 5, 2016.

Levin et al.; U.S. Appl. No. 15/017,260 entitled "Devices and Methods for Treatment of Heart Failure by Splanchnic Nerve Ablation," filed Feb. 5, 2016.

(56) References Cited

OTHER PUBLICATIONS

Adamopoulos et al; Comparison of different methods for assessing sympathovagal balance in chronic congestive heart failure secondary to coronary artery disease; The American Journal of Cardiology; 70(20); pp. 1576-1582; Dec. 15, 1992.

Andren-Sandberg et al.; Thoracoscopic splanchnicectomy for chronic, severe pancreatic pain; In Seminars in Laparoscopic Surgery; 3(1); Sage CA: Thousand Oaks CA; Sage Publications; pp. 29-33; Mar. 1, 1996.

Barnes et al.; Haemodynamic responses to stimulation of the splanchnic and cardiac sympathetic nerves in the anaesthetized cat; The Journal of Physiology; 378; pp. 417-436; Sep. 1986.

Bauereisen et al.; The importance of mesenteric mechanoreceptors for the reflex innervation of resistance blood vessels capacity blood vessels in the splanchnic area; Pflugers Archiv fur die gesamte Physiologie des Menschen und der Tiere; 276; pp. 445-455; Jan. 1963.

Bradley et al.; Nerve blocks and neuroablative surgery for chronic pancreatitis; World J. Surg.; 27(11); pp. 1241-1248; Nov. 1, 2003.

Brunner et al.; Carotid sinus baroreceptor control of splanchnic resistance and capacity. Am J Physiol.; 255; pp. H1305-H1310; Dec. 1988.

Buscher et al.; Limited effect of thoracoscopic splanchnicectomy in the treatment of severe chronic pancreatitis pain; a prospective long-term analysis of 75 cases; Surgery; 143(6); pp. 715-722; Jun. 30, 2008.

Carneiro et al.; Change in liver blood flow and blood content in dogs during direct and reflex alteration of hepatic sympathetic nerve activity; Circulation Research; 40(2); pp. 150-158; Feb. 1, 1977.

Cuschieri et al.; Bilateral endoscopic splanchnicectomy through a posterior thoracoscopic approach; Journal of the Royal College of Surgeons of Edinburgh; 39(1); pp. 44-47; Feb. 1994.

Diedrich et al.; Segmental orthostatic fluid shifts; Clinical autonomic research;14(3); pp. 146-147; Jun. 2004.

Edwards; The glycogenolytic response to stimulation of the splanchnic nerves in adrenalectomized calves, sheep, dogs, cats and pigs; J Physiol.; 213; pp. 741-759; Mar. 1971.

Eisenberg et al.; Neurolytic celiac plexus block for treatment of cancer pain: A meta-analysis; Anesth Analg; 80(2); pp. 290-295; Feb. 1995.

Ferrara et al; Hemodynamics of the splanchnic and systemic circulation after hypotonic water load-comparison between normal subjects and patients with congestive heart failure; Acta Cardiologica; 38(2); pp. 81-88; Dec. 1982.

Folkow et al.; The Effect of Graded Vasoconstrictor Fibre Stimulation on the Intestinal Resistance and Capacitance Vessels; Acta physiologica Scandinavica; 61; pp. 445-457; Aug. 1964.

Foss et al.; Reversal of genetic salt-sensitive hypertension by targeted sympathetic ablation; Hypertension; 61(4); pp. 806-811; Apr. 1, 2013.

Francis et al.; Clinical notes, suggestions and new instrument; JAMA; 134 (1); pp. 20-21; May 3, 1947.

Garcea et al.; Percutaneous splanchnic nerve radiofrequency ablation for chronic abdominal pain; Anz Journal of Surgery; 75(8); pp. 640-644; Aug. 1, 2005.

Giraudo et al.; Endoscopic palliative treatment of advanced pancreatic cancer: Thoracoscopic splanchnicectomy and laparoscopic gastrojejunostomy; Annals of Oncology; 10(4); pp. S278-S280; Jan. 1, 1999.

Goldblatt et al.; Studies on experimental hypertension II: The effect of resection of splanchnic nerves on experimental renal hypertension; The Journal of Experimental Medicine; 65(2); pp. 233-241; Feb. 1, 1937.

Goroszeniuk et al.; Permanent percutaneous splanchnic nerve neuromodulation for management of pain due to chronic pancreatitis: A case report; Neuromodulation; ;14(3); pp. 253-257; May-Jun. 2011.

Greenway et al.; Role of splanchnic venous system in overall cardiovascular homeostasis; In Federal Proceedings; 42(6); pp. 1678-1684; Apr. 1983.

Greenway; Blockade of reflex venous capacitance responses in liver and spleen by hexamethonium, atropine, and surgical section; Canadian journal of physiology and pharmacology; 69(9); pp. 1284-1287; Sep. 1991.

Griffith et al.; The vasomotor control of the liver circulation; American Journal of Physiology; 95(1); pp. 20-34; Oct. 1930.

Griffith et al.; Vasomotor Control of the Liver Circulation. Proceedings of the Society for Experimental Biology and Medicine; 27(7); pp. 673-674; Apr. 1930.

Herman et al.; Splenic afferents and some of their reflex responses; American Journal of Physiology—Regulatory, Integrative and Comparative Physiology; 242(3); pp. R247-R254; Mar. 1982.

Ihse et al.; Bilateral thoracoscopic splanchnicectomy: effects on pancreatic pain and function; Annals of Surgery; 230(6); pp. 785-791; Dec. 1, 1999.

Ischia et al; A new approach to the neurolytic block of the coeliac plexus: the transaortic technique; Pain; 16(4); pp. 333-341; Aug. 31, 1983.

Johnson et al.; An open randomized comparison of clinical effectiveness of protocol-driven opioid analgesia, celiac plexus block or thoracoscopic splanchnicectomy for pain management in patients with pancreatic and other abdominal malignancies; Pancreatology; 9(6); pp. 755-763; Jan. 1, 2009.

Kang et al.; Bilateral thoracoscopic splanchnicectomy with sympathectomy for managing abdominal pain in cancer patients; Am J Surg; 194(1); pp. 23-29; Jul. 2007.

Katri et al.; Thoracoscopic splanchnicectomy for pain control in irresectable pancreatic cancer; Journal of Laparoendoscopic and Advanced Surgical Techniques; 18(2); pp. 199-203; Apr. 1, 2008.

Kaufman et al.; Effect of portal hypertension on splenic blood flow, intrasplenic extravasation and systemic blood pressure; American Journal of Physiology—Regulatory, Integrative and Comparative Physiology; 284 (6); pp. R1580-R1585; Jun. 1, 2003.

King et al.; Splanchnic circulation is a critical neural target in angiotensin II salt hypertension in rats; Hypertension; 50(3); pp. 547-556; Sep. 2007.

Krishna et al.; Video-assisted thoracoscopic sympathectomy-splanchnicectomy for pancreatic cancer pain; Journal of Pain and Symptom Management; 22(1); pp. 610-616; Jul. 1, 2001.

Lang-Lazdunski et al.; Videothoracoscopic splanchnicectomy for intractable pain from adrenal metastasis; Ann Thorac Surg; 73(4); pp. 1290-1292; Apr. 2002.

Le Pimpec Barthes; Thoracoscopic splanchnicectomy for control of intractable pain in pancreatic cancer; The Annals of Thoracic Surgery; 65(3); pp. 810-813; Mar. 31, 1998.

Leksowski; Thoracoscopic splanchnicectomy for the relief of pain due to chronic pancreatitis; Surg Endosc.; 15(6); pp. 592-596; Jun. 2001.

Lica et al.; Thoracoscopic left splanchnicectomy—role in pain control in unresectable pancreatic cancer. Initial experience; Chirurgia; 109(3); pp. 313-317; May-Jun. 2014.

Lieberman et al.; Celiac plexus neurolysis with the modified transaortic approach; Radiology; 175(1); pp. 274-276; Apr. 1990.

Lillemoe et al; Chemical splanchnicectomy in patients with unresectable pancreatic cancer. A prospective randomized trial; Annals of Surgery; 217(5); pp. 447-457; May 1, 1993.

Lin et al.; Bilateral thoracoscopic lower sympathetic-splanchnicectomy for upper abdominal cancer pain. The European journal of surgery; Supplement 572; pp. 59-62; 1994.

Lonroth et al.; Unilateral left-side thoracoscopic sympathectomy for visceral pain control: a pilot study; The European Journal of Surgery; 163(2); pp. 97-100; Feb. 1, 1997.

Maass-Moreno et al.; Carotid baroreceptor control of liver and spleen volume in cats; Am J Physiol; 260(1 Pt 2); pp. H254-H259; Jan. 1991.

Maher et al.; Thoracoscopic splanchnicectomy for chronic pancreatitis pain; Surgery; 120(4); pp. 603-610; Oct. 1996.

Myhre et al.; Monitoring of celiac plexus block in chronic pancreatitis; Pain; 38(3); pp. 269-274; Sep. 1989.

Nakazato et al; Extrinsic innervation of the canine abdominal vena cava and the origin of cholinergic vasoconstrictor nerves; J. Physiol.; 328; pp. 191-203; Jul. 1982.

(56) References Cited

OTHER PUBLICATIONS

Pan et al.; Differential responses of regional sympathetic activity and blood flow to visceral afferent stimulation; Am J Physiol Regul Integr Comp Physiol.; 280(6); pp. R1781-R1789; Jun. 2001.

Pietrabissa et al.; Thoracoscopic splanchnicectomy for pain relief in unresectable pancreatic cancer; Archives of Surgery; 135(3); pp. 332-335; Mar. 1, 2000.

Plancarte et al.; Management of chronic upper abdominal pain in cancer: transdiscal blockage of the splanchnic nerves; Regional Anesthesia and Pain Medicine; 35(6); pp. 500-506; Nov. 1, 2010.

Prasad et al.; Thoracoscopic splanchinicectomy as a palliative procedure for pain relief in carcinoma pancreas; Journal of Minimal Access Surgery; 5(2); pp. 37-39; (Author Manuscript); Apr. 1, 2009.

Raj; Celiac plexus/splanchnic nerve blocks; Techniques in Regional Anesthesia and Pain Management; 5(3); pp. 102-115; Jul. 2001.

Raj et al.; Radiofrequency lesioning of splanchnic nerves; Pain Practice; 2(3); pp. 242-247; Sep. 2002.

Saenz et al.; Thoracoscopic splanchicectomy for pain control in patients with unresectable carcinoma of the pancreas; Surgical Endoscopy; 14(8); pp. 717-720; Aug. 1, 2000.

Sastre et al.; Transhiatal bilateral splanchnicotomy for pain control in pancreatic cancer: basic anatomy, surgical technique, and immediate results in fifty-one cases; Surgery; 111(6); pp. 640-646; Jun. 1992.

Scott-Douglas et al.; Effects of acute volume loading and hemorrhage on intestinal vascular capacitance: a mechanism whereby capacitance modulates cardiac output; Can. J. Cardiol.; 18(5); pp. 515-522; May 5, 2002.

Shimada et al.; Clinical evaluation of transhiatal bilateral splanchnicotomy for patients with intractable supramesenteric pain; Surgery Today; 29(11); pp. 1136-1140; Nov. 1999.

Smigielski et al.; Assessment of quality of life in patients with non-operated pancreatic cancer after videothoracoscopic splanchnicectomy; Videosurgery and Other Miniinvasive Techniques; 6(3); pp. 132-137; Sep. 1, 2011.

Stefaniak et al.; A comparison of two invasive techniques in the management of intractable pain due to inoperable pancreatic cancer; European Journal of Surgical Oncology; 31(7); pp. 768-773; Sep. 30, 2005.

Yan et al.; Neurolytic celiac plexus block for pain control in unresectable pancreatic cancer; Am J Gastroenterol; 102(2); pp. 430-438; Feb. 2007.

Takahashi et al.; Thoracoscopic splanchnicectomy for the relief of intractable pain; Surgical Endoscopy; 10(1); pp. 65-68; Jan. 1, 1996.

Tavassoli et al.; Thoracoscopic splanchnicectomy for pain control in urresectable pancreatic cancer; Journal of Cardio-Thoracic Medicine; 1(2); pp. 53-56; Aug. 6, 2013.

Tsybenko et al.; Central nervous control of hepatic circulation; J Aut Nery Sys; 33(3); pp. 255-266; May 1991.

Van Vliet et al.; Time course of renal responses to greater splanchnic nerve stimulation; American Journal of Physiology Regulatory, Integrative and Comparative Physiology; 260(5); pp. R894-R905; May 1991.

Verhaegh et al.; Percutaneous radiofrequency ablation of the splanchnic nerves with chronic pancreatitis: results of single and repeated procedures in 11 patients; Pain Practice; 13(8); pp. 621-626; (Author Manuscript); Nov. 1, 2013.

Wilkins et al.; The effect of splanchnic sympathectomy in hypertensive patients upon estimated hepatic blood flow in the upright as contrasted with the horizontal position; Journal of Clinical Investigation; 30(3); pp. 312-317; Mar. 1951.

Worsey et al.; Thoracoscopic pancreatic denervation for pain control in irrsectable pancreatic cancer; British Journal of Surgery; 80(8); pp. 1051-1052; Aug. 1, 1993.

\* cited by examiner

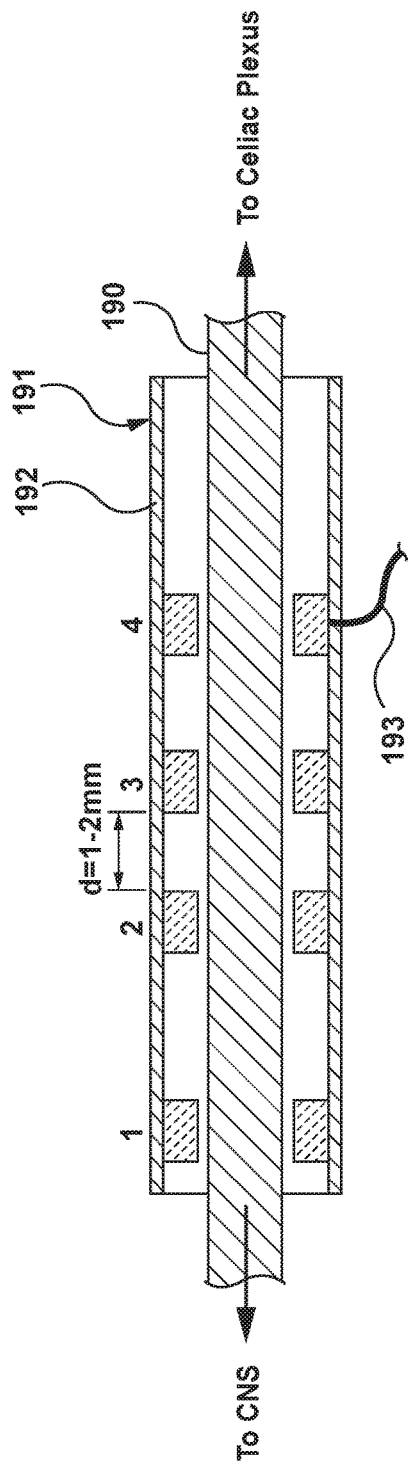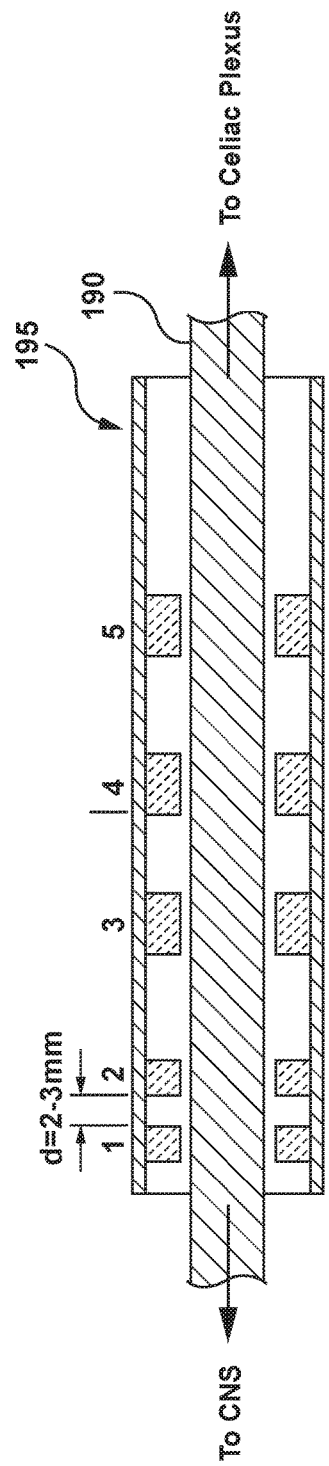
FIG. 12A
FIG. 12B

DEVICES AND METHODS FOR TREATMENT OF HEART FAILURE VIA ELECTRICAL MODULATION OF A SPLANCHNIC NERVE

CROSS REFERENCE TO RELATED APPLICATIONS

This application claims the benefit of the filing date of U.S. Provisional Application No. 62/240,864, filed Oct. 13, 2015, which application is incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present disclosure is directed generally to devices, systems and methods for treating patients suffering from heart failure by electrically modulating a greater splanchnic nerve.

BACKGROUND

Heart failure (HF) is a medical condition that occurs when the heart is unable to pump sufficiently to sustain the organs of the body. Heart failure is a serious condition and affects millions of patients in the United States and around the world.

In the United States alone, about 5.1 million people suffer from heart failure and according to the Center for Disease Control, the condition costs the nation over $30 billion in care, treatments, medications, and lost production.

The normal healthy heart is a muscular pump that is, on average, slightly larger than a fist. It pumps blood continuously through the circulatory system to supply the body with oxygenated blood. Under conditions of heart failure, the weakened heart cannot supply the body with enough blood and results in cardiomyopathy (heart muscle disease) characterized by fatigue and shortness of breath, making even everyday activities such as walking very difficult.

Oftentimes, in an attempt compensate for this dysfunction, the heart and body undergo physiological changes that temporarily mask the inability of the heart to sustain the body. These changes include the enlargement of heart chamber, increased cardiac musculature, increased heart rate, raised blood pressure, poor blood flow, and imbalance of body fluids in the limbs and lungs.

One common measure of heart health is left ventricular ejection fraction (LVEF) or ejection fraction. By definition, the volume of blood within a ventricle immediately before a contraction is known as the end-diastolic volume (EDV). Likewise, the volume of blood left in a ventricle at the end of contraction is end-systolic volume (ESV). The difference between EDV and ESV represents the stroke volume (SV). SV describes the volume of blood ejected from the right and left ventricles with each heartbeat. Ejection fraction (EF) is the fraction of the end-diastolic volume that is ejected with each beat; that is, it is stroke volume (SV) divided by end-diastolic volume (EDV). Cardiac Output (CO) is defined as the volume of blood pumped per minute by each ventricle of the heart. CO is equal to SV times the heart rate (HR). Cardiomyopathy, in which the heart muscle becomes weakened, stretched, or exhibits other structural problems, can be further categorized into systolic and diastolic heart failure based on ventricular ejection fraction.

Systolic dysfunction is characterized by a decrease in myocardial contractility. A reduction in the left ventricular ejection fraction (LVEF) results when myocardial contractility is decreased throughout the left ventricle. CO is maintained in two ways: left ventricular enlargement results in a higher stroke volume and an increase in contractility as a result of the increased mechanical advantage from stretching the heart. However, these compensatory mechanisms are eventually exceeded by continued weakening of the heart and CO decreases resulting in the physiologic manifestations of heart failure. The left side of the heart cannot pump with enough force to push a sufficient amount of blood into the systemic circulation. This leads to fluid backing up into the lungs and pulmonary congestion. In general terms, systolic dysfunction is defined as an LVEF less than 40% and heart failure in these patients can be broadly categorized as heart failure with reduced ejection fraction (HFrEF).

On the other hand, diastolic dysfunction refers to cardiac dysfunction in which left ventricular filling is abnormal and is accompanied by elevated filling pressures. In diastole, while the heart muscle is relaxed the filling of the left ventricle is a passive process that depends on the compliance (defined by volume changes over pressure changes), or distensibility, of the myocardium or heart muscle. When the ventricles are unable to relax and fill, the myocardium may strengthen in an effort to compensate to poor stroke volume. This subsequent muscle hypertrophy leads to even further inadequate filling. Diastolic dysfunction may lead to edema or fluid accumulation, especially in the feet, ankles, and legs. Furthermore, some patients may also have pulmonary congestion as result of fluid buildup in the lungs. For patients with heart failure but without systolic dysfunction, diastolic dysfunction is the presumed cause. Diastolic dysfunction is characteristic of not only hypertrophic cardiomyopathy (HCM) characterized by the thickening of heart muscle, but also restrictive cardiomyopathy (RCM) characterized by rigid heart muscle that cannot stretch to accommodate passive filling. In general terms, diastolic dysfunction is defined as an LVEF of greater than 40% and heart failure in these patients can be broadly categorized as heart failure with preserved ejection fraction (HFpEF).

While a number of drug therapies are successfully targeting systolic dysfunction and heart failure with reduced ejection fraction (HFrEF), drug therapies may have pervasive side effects in some patients and are ineffective or dangerous to others. For the large group of patients with diastolic dysfunction and heart failure with preserved ejection fraction (HFpEF) no promising therapies have yet been identified. The clinical course for patients with both HFrEF and HFpEF is significant for recurrent presentations of acute decompensated heart failure (ADHF) with symptoms of dyspnea, decreased exercise capacity, peripheral edema etc. Recurrent admissions for ADHF utilize the largest part of current health care resources and could continue to generate enormous costs.

While the physiology of heart failure is increasingly becoming better understood, modern medicine has, thus far, failed to develop new therapies for chronic management of HF or recurrent ADHF episodes. Over the past few decades, strategies of ADHF management and prevention have and continue to focus on the classical paradigm that salt and fluid retention is the culprit of intravascular fluid expansion and cardiac decompensation. Increasing evidence suggests that fluid homeostasis and control of intravascular fluid distribution is disrupted in patients with HF. Deregulation of this key cardiovascular regulatory component could not only explain findings in chronic HF but also in ADHF. Consequently, blocking of the autonomic nervous system to alter fluid distribution in the human body could be used as a therapeutic intervention.

Additionally, the classical understanding of HF pathophysiology emphasizes the mechanism of poor forward flow (i.e., low cardiac output), resulting in neurohumoral, or sympathetic nervous system (SNS) up-regulation. However, new evidence emphasizes the concurrent role of backward failure (i.e., systemic congestion) in the pathophysiology and disease progression of HF. Coexisting renal dysfunction with diuretic resistance often complicates the treatment of HF and occurs more frequently in patients with increased cardiac filling pressures. Chronic congestive HF is characterized by longstanding venous congestion and increased neurohumoral activation. Critically important has been the identification of the splanchnic vascular bed as a major contributor to blood pooling and cardiac physiology. Newly evolving methods and devices involving sympathetic nervous system blocking and manipulation of systems including the splanchnic vascular bed have opened novel avenues to approach the treatment of heart disease. In particular, the role of sympathetic nerves that innervate smooth muscle in the walls of splanchnic veins have become better known. In the case of hyperactivity of these nerves they became a novel target in the treatment of CHF.

SUMMARY OF THE DISCLOSURE

In view of the foregoing, it would be desirable to provide an apparatus and methods to affect neurohumoral activation for the treatment of heart failure and particularly diastolic heart failure, heart failure with preserved ejection fraction.

The present disclosure provides improved treatment options for patients suffering from heart failure by blocking or inhibiting the nerve activity of the splanchnic nerves (e.g., greater, lesser and least) that innervate organs and vasculature of the abdominal compartment and the greater splanchnic nerve (GSN) in particular. By selectively blocking activity of specific nerves, the disclosure provides methods and devices that can affect circulating blood volume, pressure, blood flow and overall heart and circulatory system functions. In this way, the present disclosure helps to introduce solutions to treat HF and particularly heart failure with preserved ejection fraction (HFpEF) based on the most contemporary physiological theories regarding heart failure.

About 5% of the total body water is located within the vasculature in the form of blood. The venous system contains approximately 70% of total blood volume and is roughly 30 times more compliant than the arterial system. Venous compliance is a measure of the ability of a hollow organ or vessel to distend and increase in volume with increasing internal pressure. A number of mechanisms are involved in regulation of volume, most importantly the neurohormonal system. On the arterial side, resistance vessels regulate flow and resistance. The sympathetic nervous system plays a major role in determining systemic vascular resistance predominantly through activation and deactivation of cardiopulmonary and arterial baroreflexes, as well as through changes in circulating norepinephrine. Capacitance is a determinant of the venous vascular function and higher vascular capacitance means more blood can be stored in the respective vasculature. The autonomic nervous system is the main regulatory mechanism of vascular capacitance.

Circulating blood is distributed into two physiologically but not anatomically separate compartments: the "venous reservoir" and "effective circulatory volume". The term "venous reservoir" (or "unstressed volume") refers to the blood volume that resides mainly in the splanchnic vascular bed and does not contribute to the effective circulating volume. The venous reservoir also referred to as "unstressed volume" or "vascular capacitance" can be recruited through a number of mechanisms like activation of the sympathetic nervous system, drugs, or hormones. The term "effective circulatory volume" (or "stressed volume") refers to blood that is present mainly in the arterial system and in non-splanchnic venous vessels and is one of the main determinants of preload of the heart. The stressed blood volume and systemic blood pressure are regulated by the autonomic nervous system part of which is the sympathetic nervous system.

The unstressed volume of blood is mostly contained in the splanchnic reservoir or "splanchnic vascular bed". The splanchnic reservoir consists of vasculature of the visceral organs including the liver, spleen, small and large bowel, stomach, as well as the pancreas. Due to the low vascular resistance and high capacitance the splanchnic vascular bed receives about 25% of the cardiac output and the splanchnic veins contain anywhere from 20% to 50% of the total blood volume. Consequently, the splanchnic vascular bed serves as the major blood reservoir, which can take up or release, actively and passively, the major part of any change in circulating blood volume. While experimenting with cadavers and animals, inventors were able to selectively block or stimulate the GSN to artificially manipulate or modify the venous reservoir.

Splanchnic veins are considerably more compliant than veins of the extremities. Animal and human studies demonstrate that the splanchnic reservoir can not only store considerable amounts of blood, but blood can also be actively or passively recruited from it into the systemic circulation in response to variations of the venous return to the heart. One of the main determinants of active recruitment is sympathetic nerve activity (SNA), which through hormones and a neurotransmitters epinephrine and norepinephrine causes venoconstriction, thereby reducing splanchnic capacitance and increasing effective circulatory volume. This can be explained by a large numbers of adrenergic receptors in the splanchnic vasculature that are sensitive to changes to the sympathetic nervous system. Compared with arteries, splanchnic veins contain more than 5 times the density of adrenergic terminals. The consequence is a more pronounced venous vasomotor response in the splanchnic system compared to other vascular regions.

The splanchnic vascular bed is well suited to accommodate and store large amounts of blood as well as shift blood back into active circulation, naturally acting in a temporary blood volume storage capacity. The high vascular capacitance allows the splanchnic vascular bed to maintain preload of the heart and consequently arterial blood pressure and cardiac output over a wide range of total body volume changes. Once the storage capacity of the splanchnic vascular bed is reached, increases in total body fluid express themselves as increased cardiac preload beyond physiologic need and eventually extravascular edema and particularly fluid accumulation in the lungs that is a symptom common in heart failure.

Increased activation of the sympathetic nervous system and the neurohormonal axis along with increases in body fluids and salts have long been debated as causes versus effects of heart failure. It has been previously suggested that in heart failure redistribution of the splanchnic reservoir, driven by increased sympathetic nerve activity to the splanchnic vascular bed leading to decreased venous compliance and capacitance, is responsible for increased intracardiac filling pressure (preload) in the absence of increases in total body salt and water. Heart failure is marked by chronic over-activity of the sympathetic nervous system and the neurohormonal axis. It is now suggested that sympathetic nerve activity and neurohormonal activation result in an increased vascular tone and consequently in decreased vascular capacitance of the splanchnic vascular bed. While peripheral vascular capacitance is unchanged in HFpEF and HFrEF compared to controls, the splanchnic vascular capacitance is decreased.

It is important to note that the so-called "acute heart failure" is initiated by a combination of two pathways: cardiac and vascular. The "cardiac pathway" is generally initiated by a low cardiac contractility reserve, while the "vascular pathway" is common to acute heart failure (AHF) that exhibits mild to moderate decrease in cardiac contractility reserve.

Notably, in acute decompensated heart failure (ADHF), which characterized by worsening of the symptoms: typically shortness of breath (dyspnea), edema, and fatigue, in a patient with existing heart disease, the cardiac filling pressures generally start to increase more than 5 days preceding an admission. While this could reflect a state of effective venous congestion following a build-up of volume, nearly 50% of patients gain only an insignificant amount of weight (<1 kg) during the week before admission. This means that in about 50% of cases, decompensated HF is not caused by externally added fluid, but rather symptoms and signs of congestion can be entirely explained by redistribution of the existing intravascular volume. Acute increases in sympathetic nervous tone due to a variety of known triggers like cardiac ischemia, arrhythmias, inflammatory activity and psychogenic stress and other unknown triggers can disrupt the body's balance and lead to a fluid shift from the splanchnic venous reservoir into the effective circulation. This results ultimately in an increase in preload and venous congestion. This explains the finding that in ADHF in both HFrEF and HFpEF was preceded by a significant increase in diastolic blood pressures.

In patients with HFpEF only small increases in diastolic pressures/preload can result in decompensation due to impaired relaxation of the ventricles. Thus patients with HFpEF are more sensitive to intrinsic or extrinsic fluid shifts.

Chronic congestive heart failure is characterized by long-standing venous congestion and increased neurohumoral activation. Like in AHF, the splanchnic vascular bed has been identified as a major contributor to HF physiology. Chronic decrease in vascular compliance makes the human body more susceptible for recurrent acute decompensation, making significant the consequences of chronic congestion of the splanchnic compartment. While the splanchnic vascular compartment is well suited to accommodate acute fluid shifts (e.g., orthostasis, exercise and dietary intake), the regulation of the splanchnic vascular bed becomes maladaptive in chronic disease states associated with increased total body volume and increased splanchnic vascular pressure.

Clinically observed effects of heart failure drug regimens like nitroglycerin and angiotension converting enzyme (ACE) inhibitors exhibit their positive effects in the treatment of HF in part through an increase in splanchnic capacitance subsequently shifting blood into the venous reservoir thereby lowering left ventricular diastolic pressure.

An orthostatic stress test (tilt test) can help to distinguish high from low vascular capacitance. Orthostatic stress causes blood shifts from the stressed volume into the unstressed volume. Veins of the extremities are less compliant than splanchnic veins, and therefore, their role as blood volume reservoirs is relatively minimal. Less known is that blood goes mostly into the splanchnic compartment, which results in a decreased preload to the right and left heart. Stimulation of the atrial and carotid baroreceptors results in an increased sympathetic tone causing splanchnic vasoconstriction. This compensatory mechanism is important, as it can rapidly shift volume from the unstressed compartment back into active circulation. The hemodynamic response to tilt in chronic congestive heart failure is atypical, as there is no significant peripheral pooling in the upright posture. While tolerance of orthostatic stress could be due to higher filling volumes, filling status alone cannot explain this phenomenon.

Acute oral or intravenous fluid challenge can also serve as a test of splanchnic vascular capacitance. The vascular capacitance determines how "full" the unstressed volume reservoir (venous reservoir) is and how much more fluid can be taken up to it in order to buffer the effective circulation (stressed volume). A fluid challenge could test the capacitance by measuring the effects of a fluid bolus on cardiac filling pressures. Patients with a "full tank", (low capacitance of venous reservoir), will not be able to buffer the hemodynamic effects of the fluid bolus as well as patients with a high capacitance in the venous reservoir. Understandably patients with HF, HFpEF and patients with increased sympathetic nerve activity will be more likely to respond to the fluid challenge with a disproportional rise in cardiac filling pressures. This could serve as a patient selection tool as well as measure of therapeutic success.

In order to target the splanchnic nerves, primarily the greater splanchnic nerve (GSN), the thoracic sympathetic trunk and celiac plexus, several invasive and minimally invasive methods can be used. Although not limited to these methods, access can be transthoracic, transabdominal, percutaneous, or video-assisted thoracoscopy.

Video-assisted thoracoscopic surgery (VATS) is a minimally invasive surgical technique that may be used to target the splanchnic nerves. The instrumentation for VATS includes the use of a camera-linked 5 mm or 10 mm fiber-optic scope, with or without a 30-degree angle of visualization, and either conventional thoracic instruments or laparoscopic instruments. Lung deflation, at least partially, on the side of the chest where VATS is being performed is a must to be able to visualize and pass instruments into the thorax; this is usually achieved with a double-lumen endo-tracheal tube that allows for single lung ventilation or a bronchial blocker delivered via a standard single-lumen endotracheal tube. The use of VATS provides direct visualization of the greater splanchnic nerve as well as the placement of cuff electrodes.

Electrical modulation, specifically in the form of kilohertz frequency range stimulation can provide the means to produce nerve block. The term "electric nerve block" is used to describe the use of electrical impulses to create a nerve block instead of the traditional method of injecting an anesthetizing agent into the site.

Electrodes can produce high frequency electrical impulses to overstimulate or block a target area or nerve, but require careful medical application to optimize outcomes. Nerves of the human body can repolarize in a fraction of a second, thus, the minimum blocking frequency is typically 1,000 to 20,000 Hz or more in some cases at amplitudes of electric current above threshold of stimulation or induced firing of the nerve. Current applied for some duration at such frequencies prevent the nerves from repolarizing and firing and instead achieve a neural blockade or nerve block. It is to be understood that stimulation of a target or target nerve is a term used to describe the modulation of nerve activity.

In the context of this disclosure, modulation describes not only stimulation to increase nerve activity, but also, more notably, stimulation to create a nerve block. Conduction of the blocking signal can be performed by a number of preferred embodiments, as described in the examples, including single, multiple, or multipole cuff electrodes that can be spiral or other cuff configurations.

In light of the foregoing, it is desired that the present disclosure provide treatment that is portable and implantable, yet effective in reliably blocking target nerves, such as the greater splanchnic nerve, to mobilize blood out of the effective circulation (stressed volume) and shift it into splanchnic organs or vasculature, and bed (venous reservoir) in order to temporarily decrease cardiac preload and reduce venous congestion, relieve pulmonary congestion, reduce pulmonary blood pressures and thus sensation of dyspnea and to increase stroke volume, enhance blood circulation and improve overall heart function. As such, use of the present disclosure would grant patients suffering from heart disease a return to a higher quality of living. This may be especially important in patients with HFpEF that have normal pulmonary blood pressures at rest but elevated ones when they attempt to exercise and are thus unable to exercise or have modest physical activity because of sensation of dyspnea that is believed to be caused by an increase of pulmonary blood pressures.

Further, the present disclosure could be used in the therapy of acute as well as chronic heart failure decompensation. Acute heart failure decompensation would be prevented or its progression halted by an offloading of the stressed volume and relieving venous congestion, which believed to be a significant component of renal dysfunction in heart failure. The disclosure can be used in support of traditional medical therapy like diuretics as it can interrupt or delay progression of cardiac decompensation.

In a chronic congestive heart failure state, the use of the disclosure can be used on a long-term basis to improve fluid distribution, thus improve symptoms of congestion like shortness of breath and improve exercise capacity.

Compared to present methods of nerve blocking, the disclosure aims to create reliable and consistent methods of nerve blocking that are safe and cause no adverse effects, such as pain, sensation or nerve damage. Additionally, the present disclosure fulfills a long desired need to provide a treatment for heart failure, especially for patients of diastolic or heart failure with preserved ejection fraction (HFpEF) and particularly the need to reduce or moderate the increase of pulmonary pressure and relieve dyspnea (shortness of breath).

BRIEF DESCRIPTION OF THE DRAWINGS

Other advantages of the disclosure are made apparent in the following descriptions taken in conjunction with the provided drawings wherein are set forth, by way of illustration and example, certain exemplary embodiments of the present disclosure wherein:

FIGS. 12A and 12B are schematic diagrams of nerve cuff configurations used to deliver blocking therapy.

DETAILED DESCRIPTION

The present disclosure relates to medical devices and methods that offer treatment of heart disease, dysfunction and heart failure, particularly HFpEF through the mechanism of increased venous capacitance and relief of pulmonary congestion. The treatments are provided through electrical block of at least a portion of a splanchnic nerve (e.g., greater splanchnic nerve, lesser splanchnic nerve, least splanchnic nerve, splanchnic nerve roots, nerve fibers connected between the thoracic sympathetic trunk and celiac plexus) with a nerve cuff electrode implanted to impede or stop communication of a nerve signal along the blocked nerve, which can affect physiological responses that are directly or indirectly involved in the numerous factors of cardiovascular health.

Figure 1:
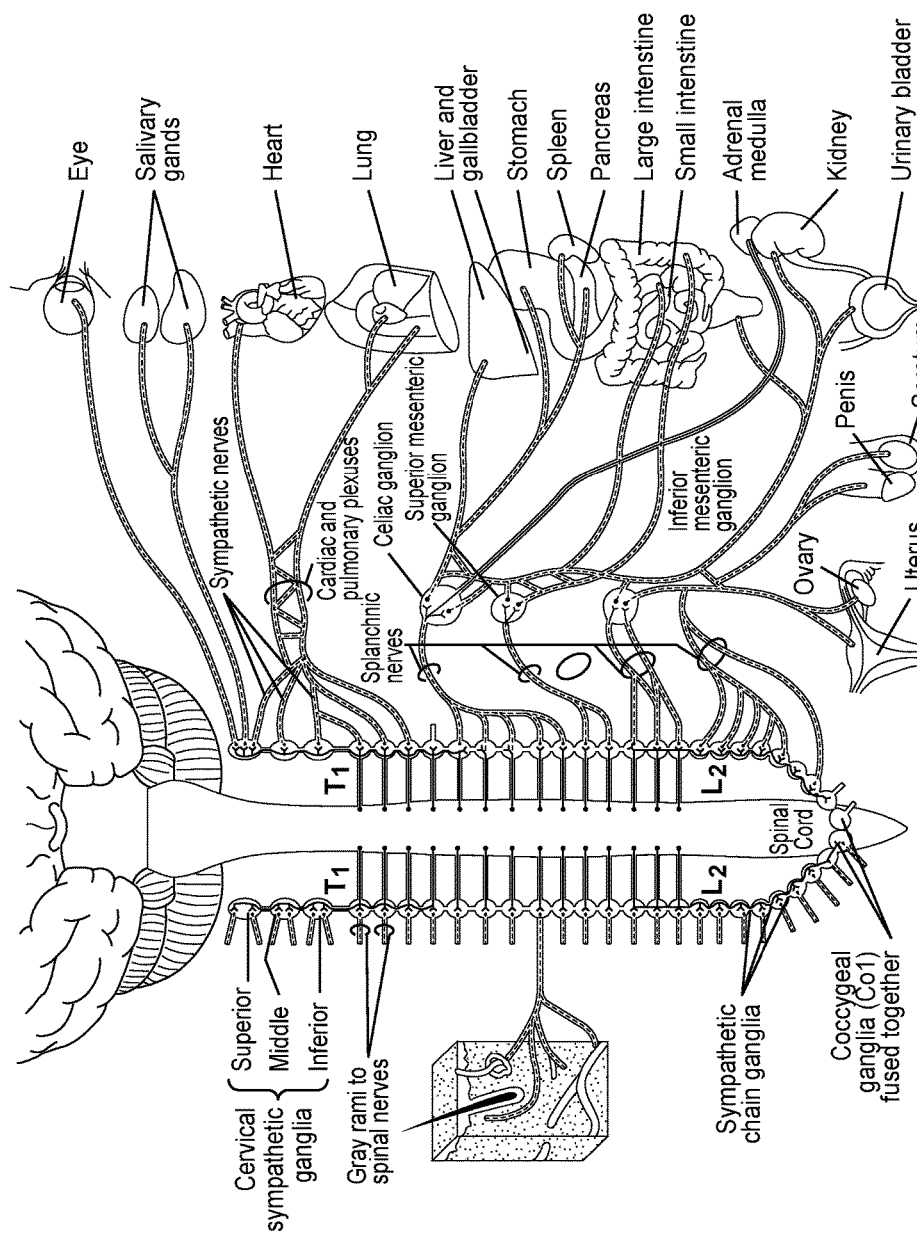
FIG. 1 is an anatomical representation of the supply of sympathetic nerve fibers to organs of the human body.

FIG. 1 is an anatomical representation of the supply of sympathetic nerve fibers to organs of the human body. The SNS is part of the autonomic nervous system, which also includes the parasympathetic nervous system.

The SNS activates what is often termed the fight or flight response. Like other parts of the nervous system, the sympathetic nervous system operates through a series of interconnected neurons. Sympathetic neurons are frequently considered part of the peripheral nervous system, although there are many that lie within the central nervous system.

Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through chemical synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation can elicit the release of adrenaline from the adrenal medulla.

Once released, noradrenaline and adrenaline bind adrenergic receptors on peripheral tissues. Binding to adrenergic receptors causes the effects seen during the fight-or-flight response. These include pupil dilation, increased sweating, increased heart rate, and increased blood pressure.

Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Thoracic splanchnic nerves (e.g., greater, lesser, or least splanchnic nerves), which synapse in the prevertebral ganglia are of particular interest for this disclosure.

Figure 2:
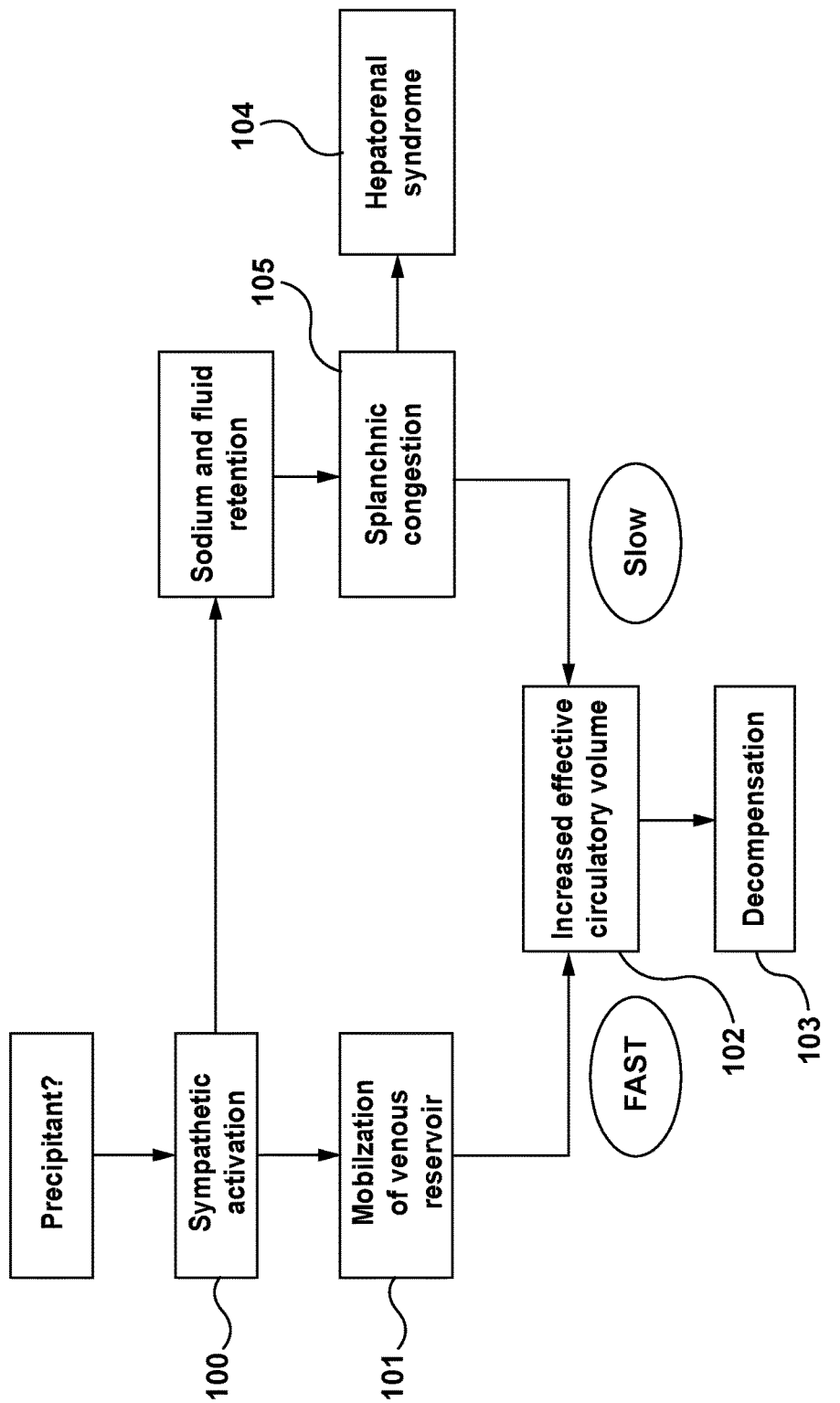
FIG. 2 is a flow diagram showing the mechanisms of decompensated heart failure

FIG. 2 is a flow diagram showing the mechanisms of decompensated heart failure. It illustrates the role of sympathetic nerve activation 100 in the mobilization of venous reservoir 101 into the effective circulatory volume 102 leading to decompensation 103. Reversing, at least partially, by ablation of a greater splanchnic nerve, the sympathetic activation of splanchnic nerves is expected to relieve HF symptoms and reduce load on the failing heart.

A particular area of interest in the body is the splanchnic compartment, splanchnic vascular bed, or splanchnic reservoir, which include the vasculature of the visceral organs including the liver, spleen, small and large bowel, stomach as well as the pancreas. The splanchnic venous vascular bed serves as the major blood reservoir and can be affected by activation (e.g., stimulation) or deactivation (e.g., blocking or ablation) of splanchnic nerves and particularly of the greater splanchnic nerve (GSN) causing relaxation of veins, mobilization, release or uptake of venous blood from or to splanchnic vascular beds, respectively, and important changes in circulating blood volume.

The GSN may at least partially control splanchnic venous compliance and capacitance. Capacitance is reduced in CHF patients and particularly in some very hard to treat HFpEF patients as a part of overall elevated sympathetic state. The sympathetic fibers in the greater splanchnic nerve bundle that control contraction of splanchnic veins are the particular target of the proposed blocking therapy. In the context of this disclosure the GSN can mean right or left greater splanchnic nerve and electrical block and stimulation can be performed via an implanted nerve cuff electrode(s) or a bilateral treatment can be performed from nerve cuff electrodes implanted to access both right and left greater splanchnic nerves. The splanchnic congestion and high venous pressure is believed to adversely affect renal function and can be illustrated by hepatorenal syndrome that causes diuretic resistance. One theory is that the high portal vein pressure is sensed by mechanoreceptors in the portal venous system and signaled via neural reflex pathways to the kidney resulting in the retention of sodium and fluid. It is believed by inventors that the proposed block may at least partially reverse this phenomenon, improve renal function and enable diuretics to work (restore diuretic responsiveness).

Figure 3:
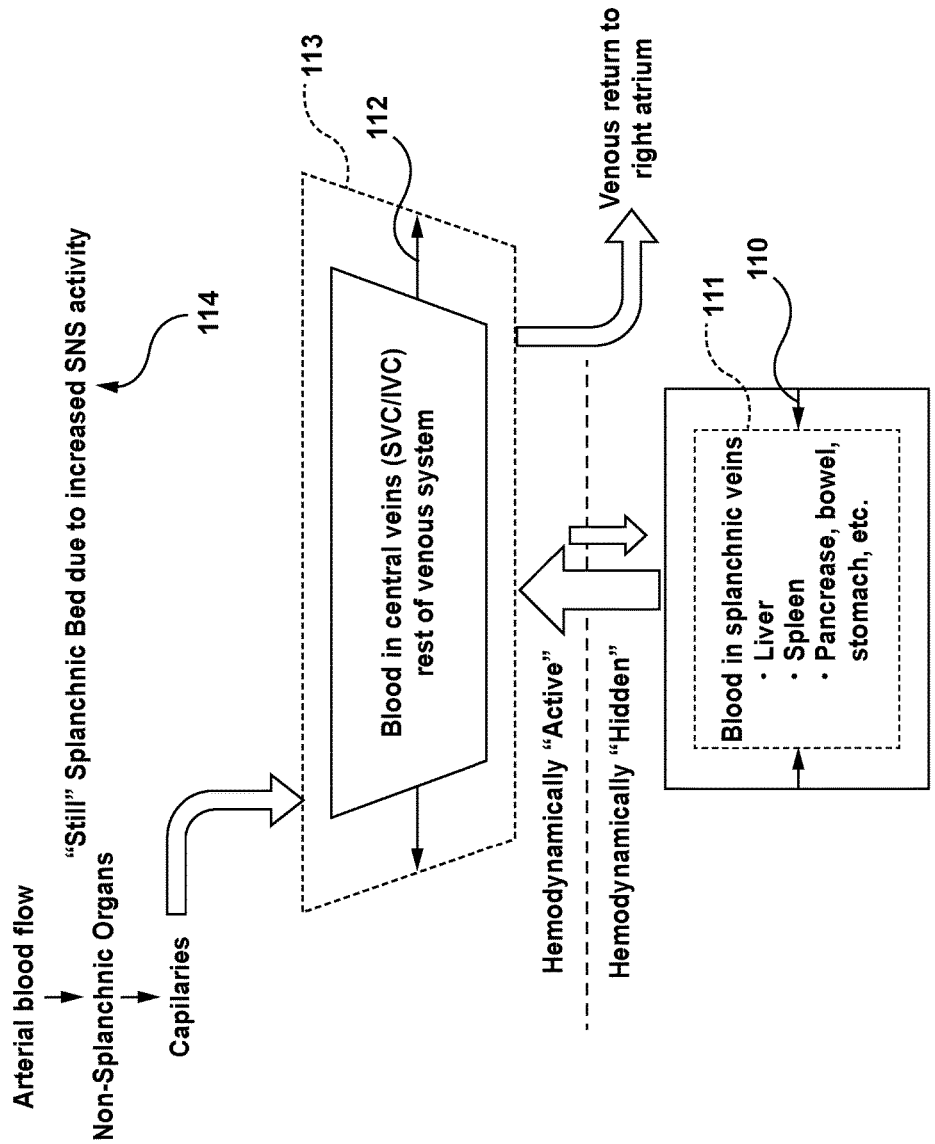
FIG. 3 is a partial flow diagram showing the role of splanchnic compartment in blood volume distribution in heart failure.
Figure 4:
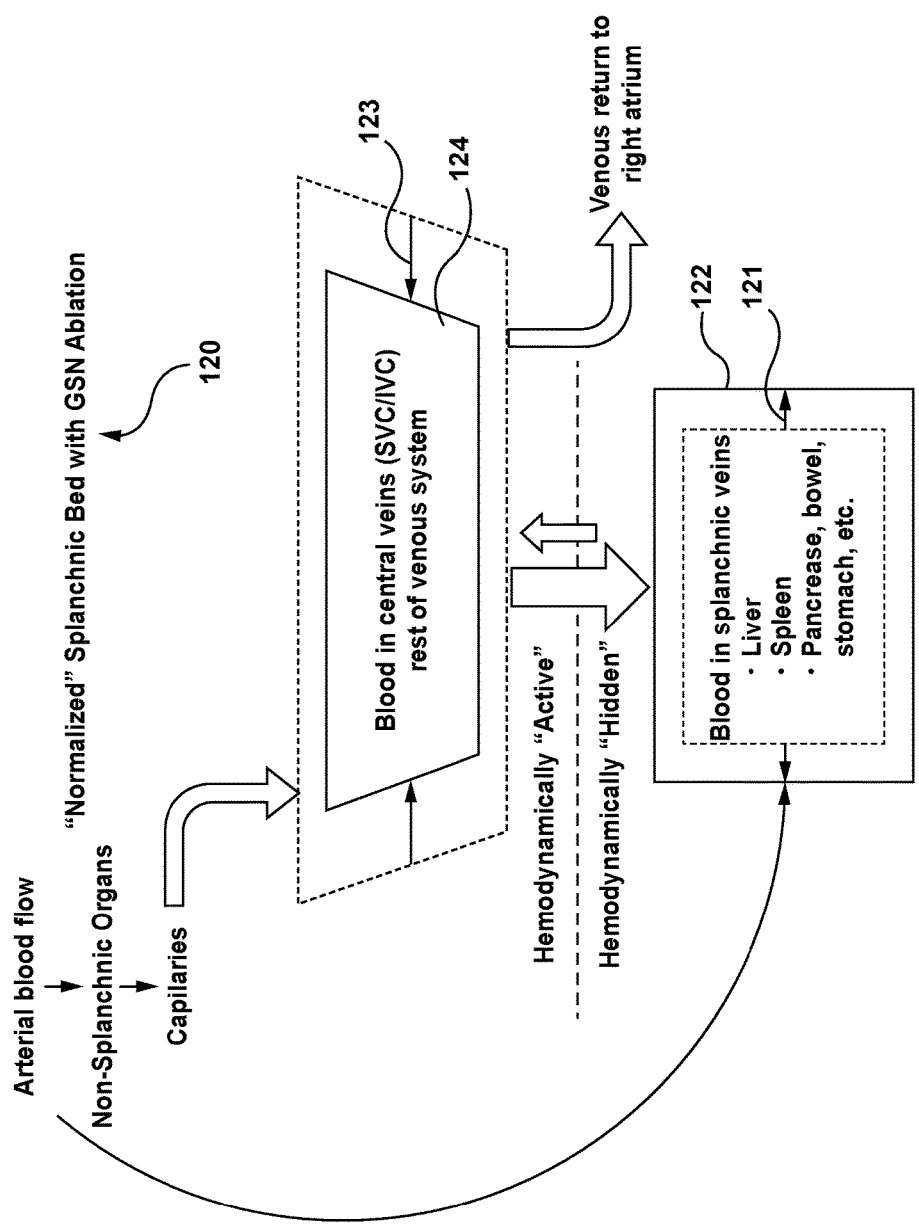
FIG. 4 is a partial flow diagram showing the role of the therapeutic effects of disclosure to heart failure.

FIG. 3 and FIG. 4 show some of the interactions between increases in sympathetic nervous system activity, including natural activity (e.g. rate of firing) of the GSN, and the storage of blood in the splanchnic bed. As illustrated by FIG. 3, increased central SNA 114, can manifest, at least partially, in the elevated activity of the GSN in all types of HF, resulting in a lower splanchnic capacitance and possibly stiffened, less-compliant splanchnic bed and regional effects including a decrease in the amount of blood stored in the splanchnic veins perfusing and surrounding the splanchnic organs (e.g., liver, spleen, pancreas, stomach, bowels) 110 and an increase in the amount of blood in central (and pulmonary) veins 112. The volume of blood in splanchnic veins or the splanchnic vascular bed 111 can be described as a "venous reservoir", or "unstressed volume" and refers to the blood volume that does not contribute to the effective circulating volume and is therefore hidden from circulation or the hemodynamically hidden blood volume. The volume of blood in central veins 113 can be termed "effective circulatory volume" or "stressed volume" and refers to blood that is present mainly in the non-splanchnic veins and is one of the main determinants of preload to the heart and in CHF can contribute to venous congestion, high pulmonary circulation pressures and sensation of dyspnea.

Conversely, as illustrated by FIG. 4, decreased sympathetic nervous system activity or a splanchnic bed normalized with GSN blocking 120 may result in the compliance of the splanchnic bed, which may be relaxed or normalized from the "stiff" or contracted state. Blocking or inhibiting a target splanchnic nerve can result in a decrease of efferent sympathetic tone to smooth muscle in the walls of veins in the splanchnic vascular bed referred to as splanchnic "venodilation" resulting in an increase 121 in the volume of blood stored in the splanchnic bed 122 and a decrease 123 of volume of blood in the central veins 124 or in the overall decrease in sympathetic nervous system activity. Other effects of GSN blocking or inhibition may comprise reduction of pulmonary vascular pressure and pulmonary capillary wedge pressure that is index of left ventricular end-diastolic pressure, which are important measurable improvements in the treatment of HF. Understanding and utilizing these interactions are some of the primary aims of several embodiments disclosed herein. Specifically, the compliance and capacitance of splanchnic vasculature is desired to be increased.

Figure 5:
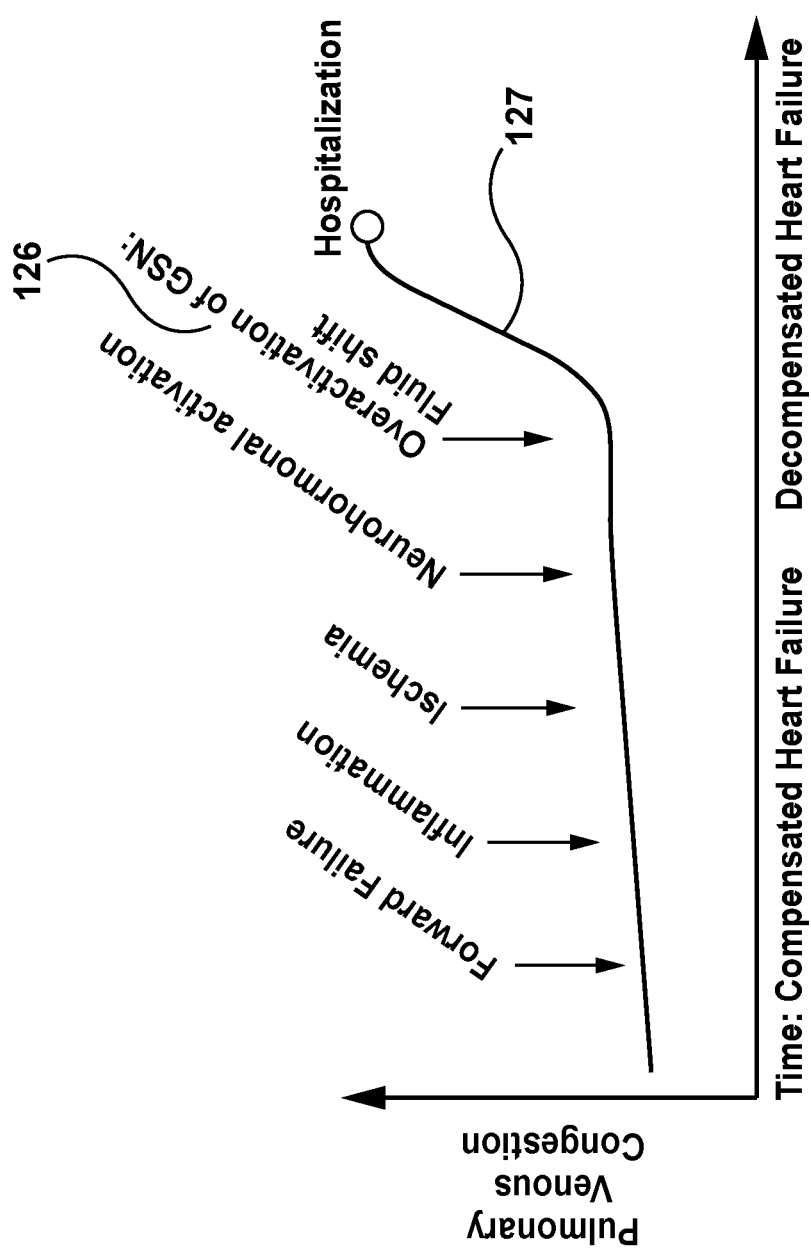
FIG. 5 is a graphical representation of pathophysiology of acute decompensated heart failure.

FIG. 5 shows one possible clinical scenario in which the sympathetic hyperactivity of the greater splanchnic 126 nerve leads to the acceleration of fluid overload 127 and pulmonary venous congestion in a HFpEF patient. Preventable hospital admission of the HF patient is precipitated by the increase of pulmonary blood pressures in response to exercise that causes "dyspnea upon exertion". This sensation can be partially explained by the patient's inability to buffer the sudden increase of venous blood volume and pressure caused by exercise that is transmitted to the pulmonary circulation and left atrium of the heart.

Figure 6A:
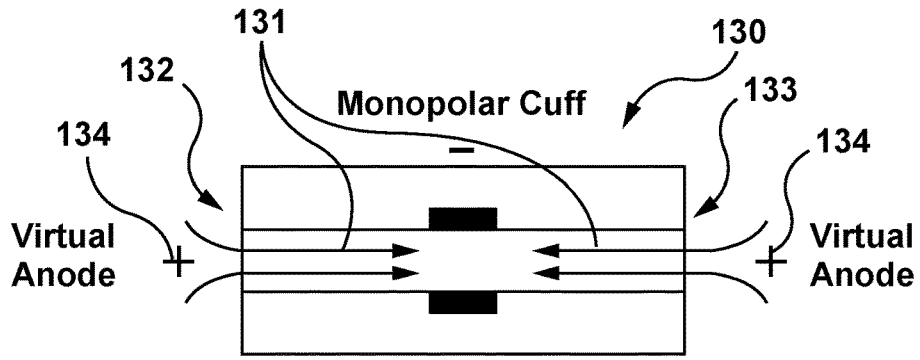
FIGS. 6A, 6B and 6C are representations of the electrical current in different cuff electrodes.
Figure 6B:
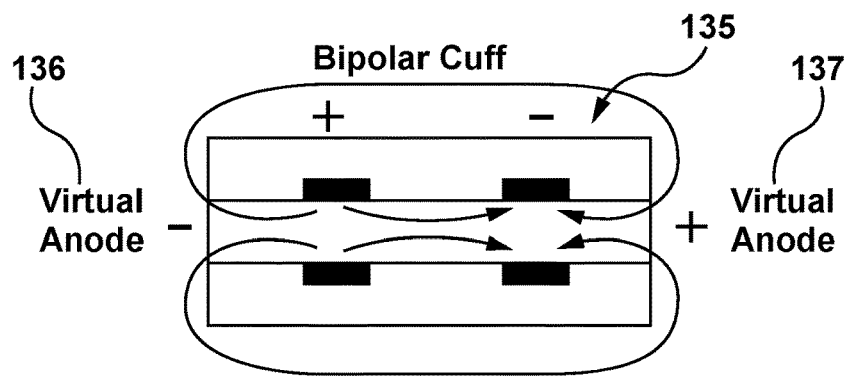
Figure 6C:
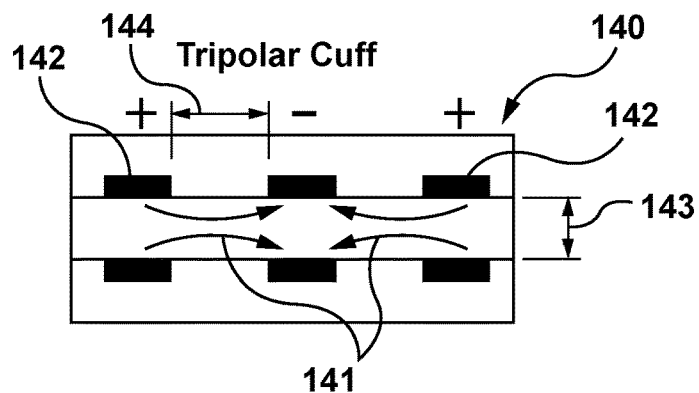

FIGS. 6A, 6B and 6C compares three different types of cuff electrodes including monopolar (FIG. 6A), bipolar (FIG. 6B), and tripolar (FIG. 6C). Electrical current paths of the compared types are shown. During high frequency biphasic stimulation (HFBS), when compared with a point electrode, the monopolar cuff electrode 130 (FIG. 6A) uses the electrical current more efficiently because the cuff limits the current flow 131 in a 2-dimensional space along a nerve. But, the electrical current coming into the monopolar cuff might not be equal on each end 132 and 133 of the cuff electrode 130, which could cause unintended stimulation at one end of the cuff. The current 131 on each side of the cuff is mainly determined by the tissue resistance on each side of the cuff and by the location of the remote reference electrode (not shown). In addition, although the reference electrode is located remotely, there is always a virtual anode 134 at each end of the cuff because the current always flows into the nerve at the cuff ends. For HFBS, the virtual anode is actually delivering HFBS at each end of the cuff causing an excitation or block depending on the stimulation intensity.

Similarly, a bipolar cuff electrode 135 (FIG. 6B) could produce a virtual anodal 136 or cathodal 137 electrode at each end of the cuff 135 depending on the tissue resistance within and around the cuff. For HFBS, these virtual electrodes could produce an unintended stimulation or blockade depending on stimulation intensity. The virtual electrodes 136 and 137 could produce variability and unpredictability in each clinical application because the tissue resistance in and around the cuff 135 could change with time. In acute animal experiments, this variability or unpredictability presented as variable blocking effects, i.e., sometimes the nerve was blocked but other times the nerve block failed depending on the blood or fluid accumulation in and around the cuff or the position of the nerve in the cuff.

The tripolar cuff electrode 140 (FIG. 6C) effectively eliminates the virtual electrode problems (e.g., associated with a monopolar cuff or bipolar cuff) by connecting the two electrodes 142 at each end of the cuff thereby forcing the potentials at each end of the cuff to be equal (i.e., no electrical current 141 can flow outside the cuff). The tripolar cuff electrode may be an efficient minimal electrode cuff configuration because it maximally utilizes the current 141 for nerve stimulation when compared to the monopolar or bipolar cuff electrode. In order to fully utilize the efficiency, the inner diameter 143 of a tripolar cuff should closely fit the diameter of a nerve it is fitted to so that less current will flow in the space between the nerve and the electrode. The electrode spacing 144 should be 1 to 2 mm in general because the internodal distance of a nerve axon is about 100 times the axon diameter. For axons of 1 to 20 µm in diameter, the internodal distances range from 0.1 mm to 2 mm. For electrical blocking of the target nerve (e.g., GSN, lesser splanchnic nerve, least splanchnic nerve, splanchnic nerve roots) that has an axon diameter less than 10 electrode spacing of 1 mm may be adequate.

Figure 7A:
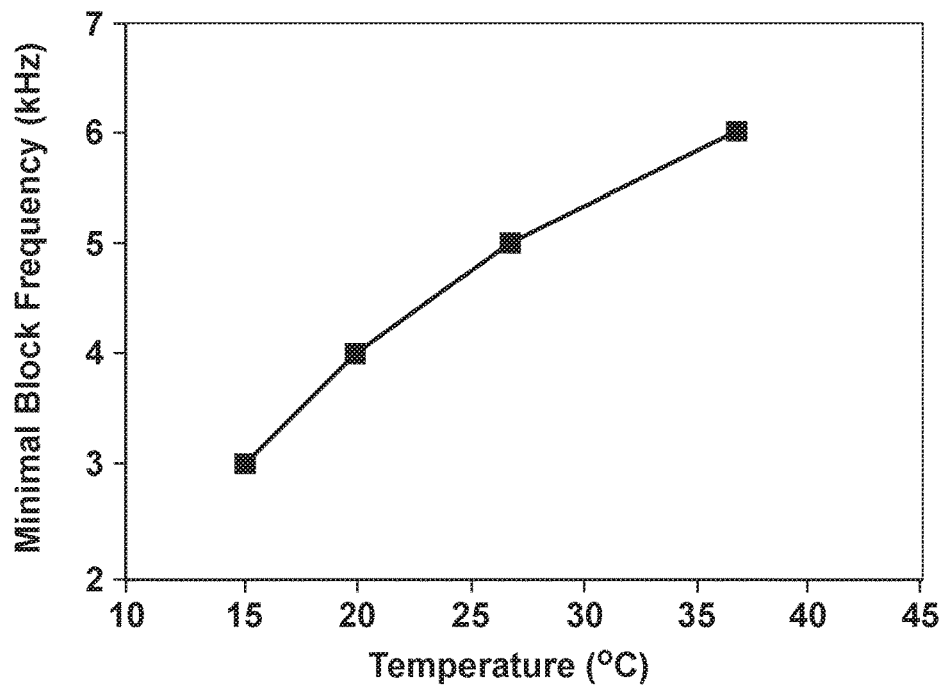
FIGS. 7A and 7B illustrate factors that determine minimal electrical blocking parameter.
Figure 7B:
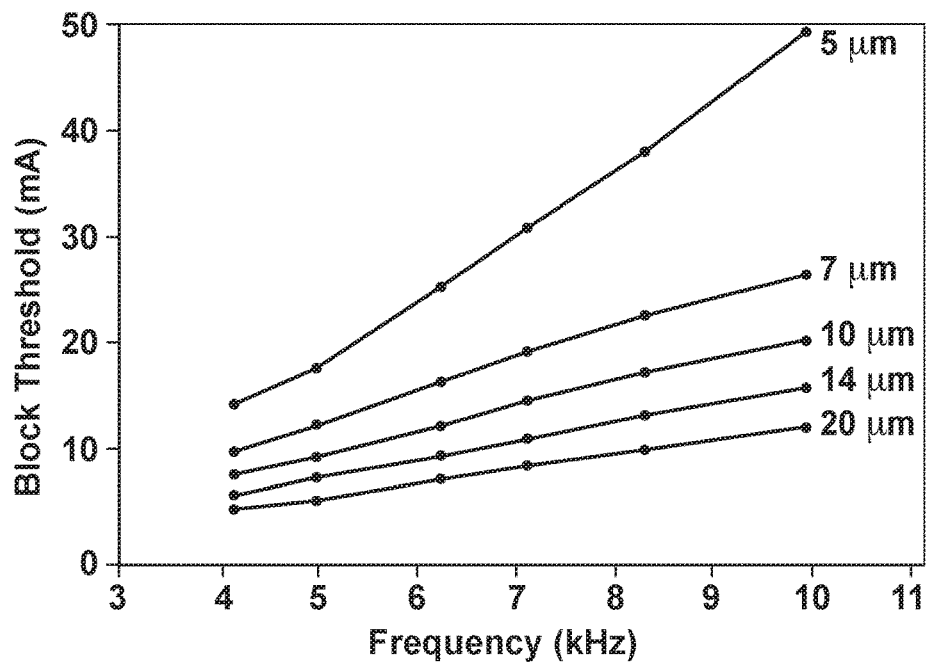

Computational modeling results suggest that the minimum frequency needed to block nerve activity is determined by potassium channel kinetics. Since it is also known that at lower temperatures ion channel kinetics become slower, the minimal blocking frequency must decrease with temperature. FIG. 7A demonstrates how changes in temperature affect the minimum electrical frequency required to block axonal conduction for a nerve having an Axon diameter of 10 µm. Thus, the minimum blocking frequency should be at least 6 kHz due to the temperature of the human body (37° C.). The minimum stimulation intensity needed to block the nerve (i.e., the block threshold) increases with increasing frequency for axons of different diameter (5 to 20 µm), see FIG. 7B.

Figure 8:
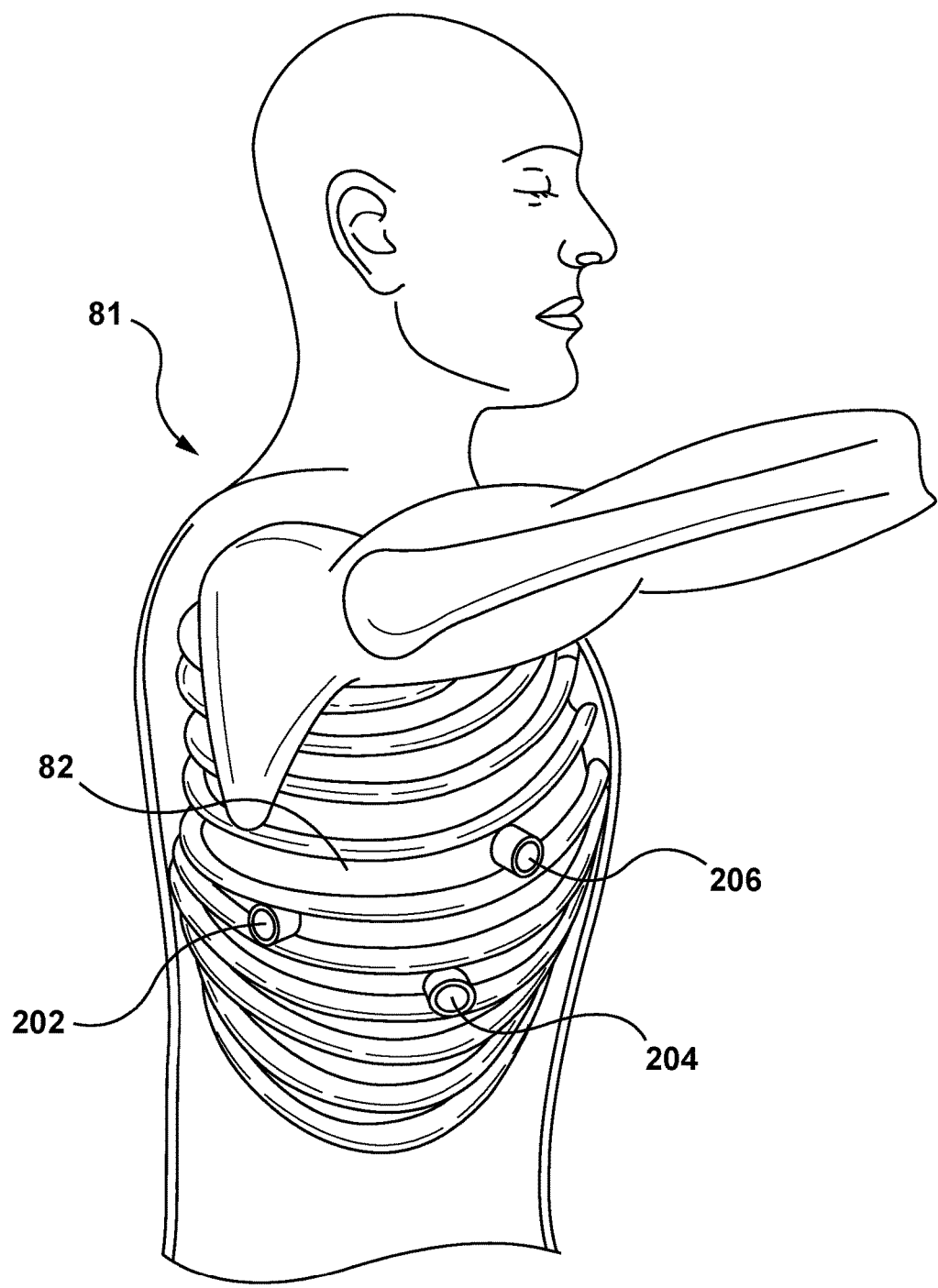
FIG. 8 is a schematic diagram of patient lying in the lateral decubitus position having one camera port in the fifth intercostal space at the mid-axillary line and one instrument port placed at the anterior axillary line.

A non-limiting example of placing a therapy delivery device on a target site of the splanchnic nerves is described. FIG. 8 is a schematic illustration of a view looking down on a patient 81 that is positioned in a lateral decubitus position. Flexion of the table allows some separation of the ribs by dropping the patient's hips and therefore increasing the intercostal space 82 to work through. The ipsilateral arm is abducted on an arm holder. Rotating the table anteriorly and using reverse Trendelenburg positioning further maximizes the exposure to the superior paravertebral area by allowing the soon to be deflated lung 87 (FIG. 9) to fall away from the apical posterior chest wall 88.

The following procedure is an example and it is understood that a skilled thoracic surgeon can modify and improve it. The procedure begins by placing patient under general anesthesia and intubated via a double lumen endotracheal tube. The double lumen endotracheal tube permits ventilation of one lung 89 and collapse of the other lung 87 on the side of the thorax that is to be operated upon without using carbon dioxide insufflation. One incision is made in the midaxillary line seventh intercostal space that is identified as port 204. Port 204, can be used for various reasons, but it is preferred that port 204 is used as a telescopic video port, which may provide video assistance during the procedure. While under endoscopic observation, a second incision is made in the fifth intercostal space at the anterior axillary line that is identified as port 206. Port 206 is preferably used as an instrument channel. A third incision is made at the posterior axillary line in the sixth intercostal space that is identified as port 202. Port 202 is preferably used as a second instrument channel. Additional ports (or fewer) can be made as needed.

Figure 9:
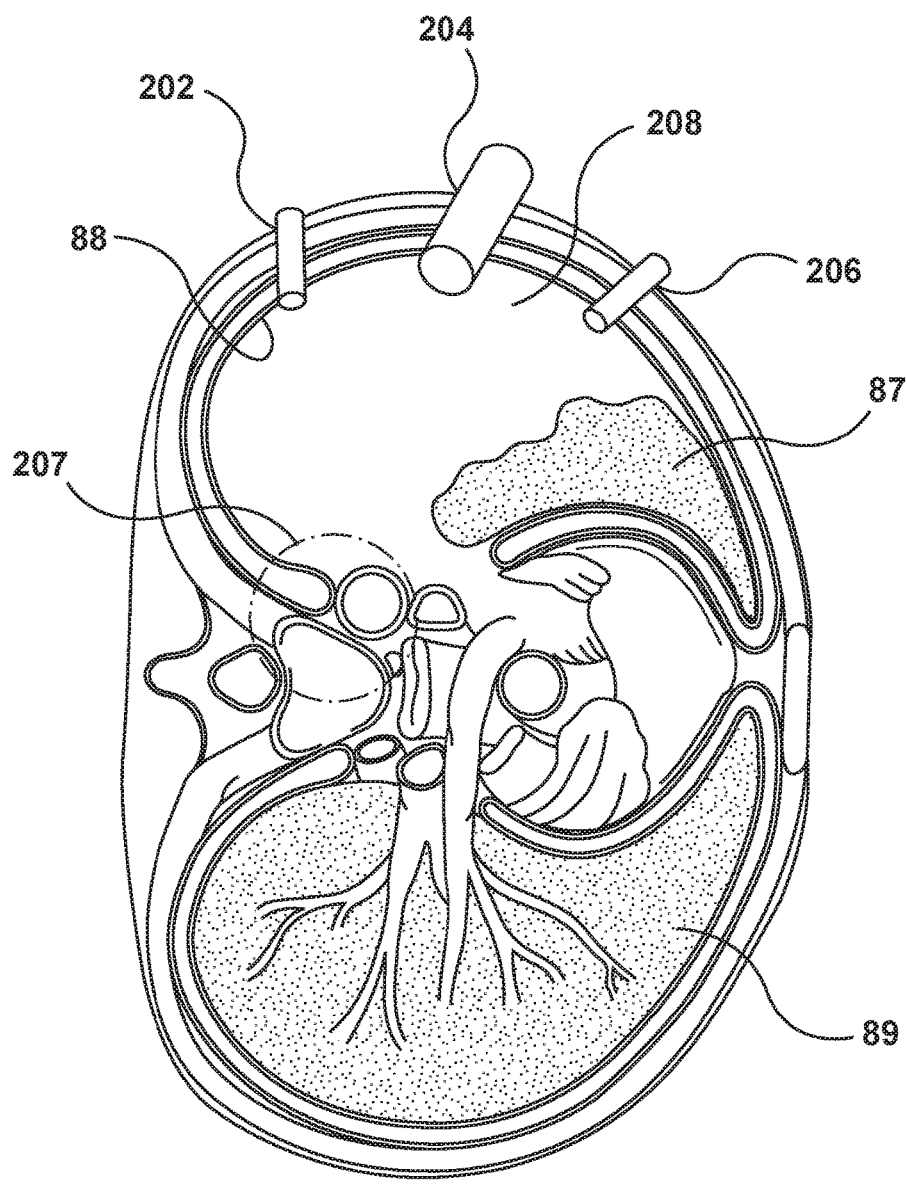
FIG. 9 is an axial cross section view of the upper thoracic region including one visualization port and two instrument ports accessing the paravertebral region where the thoracic splanchnic nerves lie.

FIG. 9 is a schematic diagram of a transverse cross section of the surgical site. The surgical exposure of an area of interest 207 and preparation of the relevant portion of the GSN for treatment is described. Visualization during the procedure may be provided by a camera introduced via a port, e.g., port 204. After the lung 87 is collapsed, and if necessary, retracted down by a fanning instrument via one of the instrument ports (e.g., port 202), the pleural cavity 208 is inspected. The entire intrathoracic sympathetic chain (not shown) can be visualized under the parietal pleura. The greater splanchnic nerve (not shown) can be visualized through the parietal pleura from its first root to the diaphragmatic recess. Before making an incision, identification of the GSN can be confirmed. A needle or hook electrode can be introduced through one of the instrument ports and manipulated to penetrate the parietal pleura proximate to the GSN. After obtaining the desired position proximate to the GSN, the hook electrode is connected to an external electrical stimulator to deliver a stimulation signal and monitor physiological response to confirm GSN stimulation.

Figure 10:
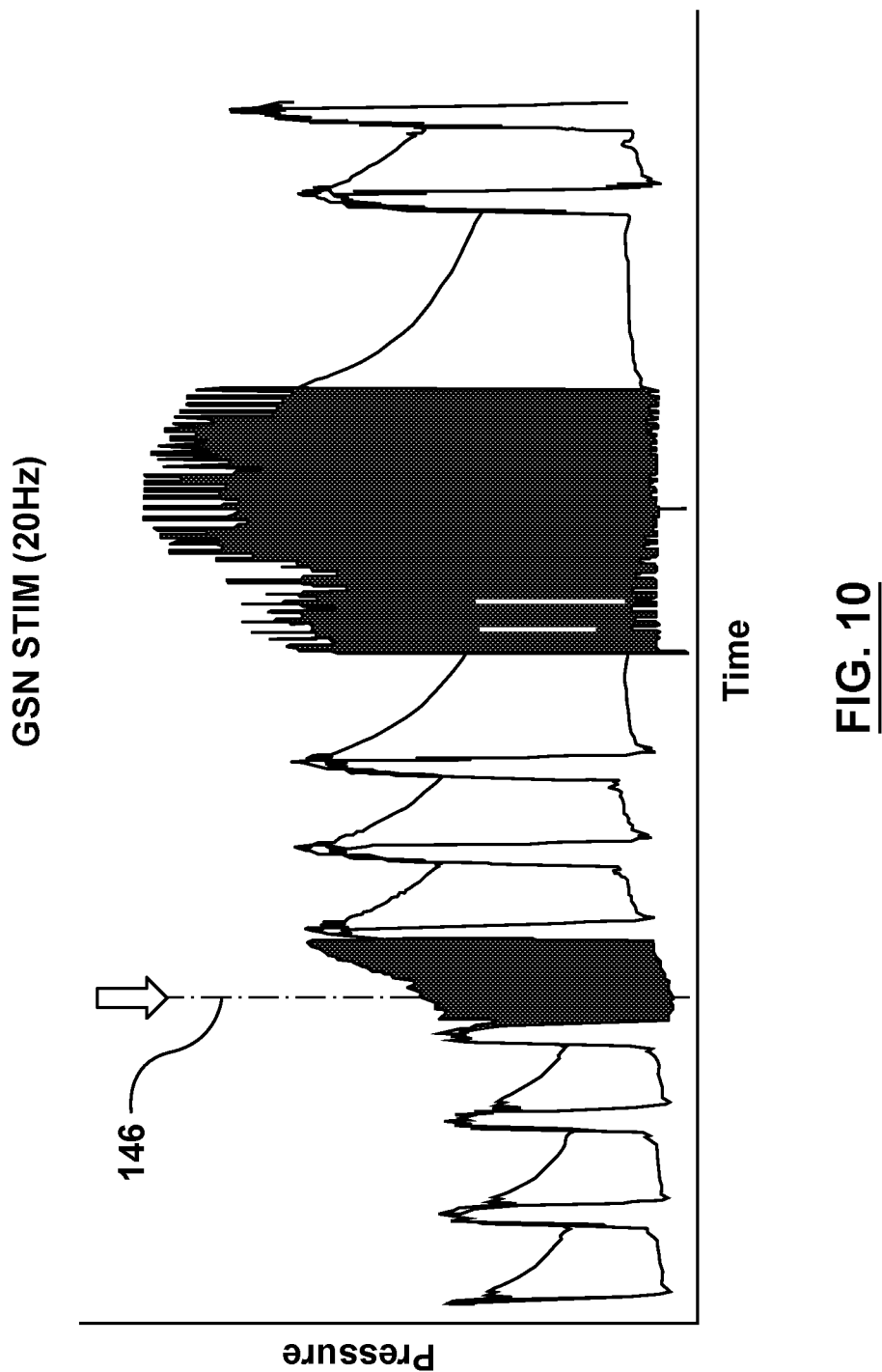
FIG. 10 is a plot of aortic and ventricular pressure in response to electrical stimulation of a GSN in an animal study.

FIG. 10 illustrates a response to stimulation 146 of a GSN at a level just above the diaphragm in an animal experiment performed by the authors. The recognizable waveforms of increased aortic and left ventricular pressure reflect the physiologic response to electrical stimulation of the GSN. Similar increases were observed in central venous pressure, right atrial pressure and pulmonary artery pressure that can be measured and monitored in real time in any well-equipped modern catheterization laboratory by a trained cardiologist or surgeon.

Figure 11:
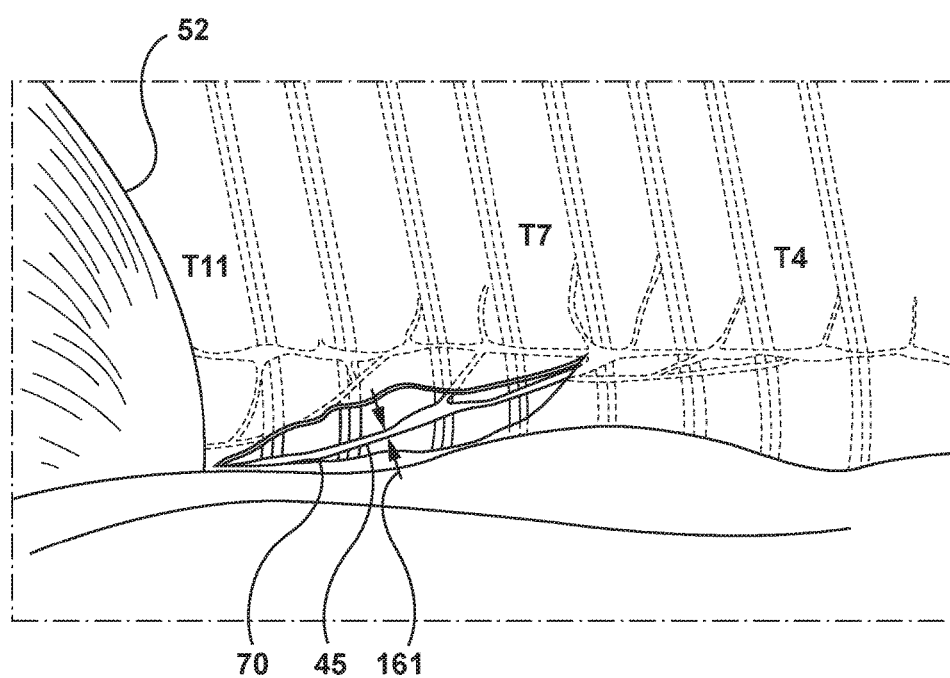
FIG. 11 is a schematic of the identification and exposure of the greater splanchnic nerve.

After confirmation of GSN identification, the GSN 45 may be exposed and dissected from the fascia. FIG. 11 is a diagram showing exposure of a GSN 45. A pleural incision 70 from the level of T7 to the diaphragm 52 along the medial aspect of the GSN 45 is shown (FIG. 11). Electrocautery should not be used near the nerve, nerve branches or the cuff electrode. Dissection of the pleura 70 and tissue on both sides of the target nerve should be performed using fine instruments. The optimal location for implantation of the cuff electrode is as close the diaphragm 52 as possible. Prior to implanting a nerve cuff electrode, the diameter 161 of the GSN should be determined. A vessel loop of a known size should be used to estimate nerve diameter. It is possible to have cuffs of several diameters available to improve the cuff fit on the nerve.

In one embodiment, a nerve cuff electrode is tripolar in configuration. It is envisioned that more than 3 electrodes can be advantageous in some embodiments. The nerve cuff diameter will be approximately the same diameter as the nerve to optimize nerve to electrode contact but minimize nerve damage. Additionally, the nerve cuff assembly may include additional cuffs (with or without electrical contacts), proximal and/or distal to the active nerve cuff. The additional cuffs may be used to serve as strain relief for the active cuff electrode and aid in maintaining alignment of the active nerve cuff.

A cuff 191 can be equipped with additional electrodes for nerve recording designed to pick up extracellular potentials that propagate along axons 190 (See FIGS. 12A and 12B). With the electrode connected to a suitable recording amplifier that can be part of the embedded electronics of the IPG (e.g., signal conditioning circuit and DAQ, see FIG. 16), a signal can be recorded whenever an action potential propagates along the nerve. The amplitude V of the recorded potential is a function of the extracellular action current amplitude, its wavelength and the length of the nerve portion that is between electrodes. Nerve potentials can be recorded if a length of nerve is encompassed by an insulating cuff with electrodes placed inside the cuff. The amplitude of the recorded signal depends non-linearly on the length of the insulated portion. To obtain maximal signal amplitudes the length of a nerve cuff should approximate wavelength to the extent possible. Since a GSN in humans can be dissected and cuffed at 2 to 4 cm of length, it is feasible. There is no further advantage to having the cuff length exceed wavelength. For large myelinated axons, optimal length ranges between 30 and 40 mm. As a rule, adequate signals are recorded during behavioral tasks when the cuff length is about 10 times greater than the cuff inside diameter. An essential prerequisite for recording nerve activity is to use an insulating cuff comprising an electrically insulating layer 192. A cuff wall permeable to electric current or an incompletely sealed cuff will allow nerve currents to leak out and, additionally, signals generated by structures outside the cuff by electromyographic (EMG) noise originating from nearby muscles and heart ECG may leak into the cuff and contaminate the recordings with unwanted noise. Therefore, cuff-recording electrodes will not be able to resolve nerve potentials from the noise unless the cuff is well sealed along its entire length.

A possible side-effect of the HFBS therapy includes undesired stimulation of muscle and pain nerves, for example, intercostal nerves and innervated fascia. In one embodiment, an isolating material may be inserted between the dissected nerve and the intercostal space. The isolating material serves to limit undesired stimulation, thus limiting possible pain associated with HFBS.

Another possible side-effect of HFBS may be a result of the initial nerve excitation during HFBS (or onset phenomenon). The mechanism by which HFBS provides its blocking action is believed to be through constantly activated potassium channels. HFBS generates an initial action potential because the potassium channel is not yet activated at the beginning of the HFBS. A possible means to limit onset phenomenon is to use a cascade of electrodes to create block of different strengths or gradually incremental partial blocks. The length of GSN available for implantation of the cuff electrode is approximately 3 to 4 cm long. Based on this, a nerve cuff with 5 to 12 or more electrodes is possible. In one embodiment, a 3 to 4 cm nerve cuff with 5 to 12 active electrodes is implanted on the GSN. Gradual HFBS of different strengths could be created. Each block could reduce conduction and onset would only come from the virtual electrodes at the edges of the cuff. The virtual electrodes proximate to the cuff edges would have less intensity, thus limiting possible side-effects from the onset phenomenon, especially on the afferent edge of the nerve where pain fibers may be a concern Regardless of the modality of nerve block, embodiments of a device and method may further be configured to assist the blocking procedure with a means to confirm safety and efficacy prior to and following blocking. A means to confirm technical efficacy may comprise identification of a target nerve before blocking and absence of a target nerve signal transmission following the blocking. A means to confirm procedural efficacy may comprise temporarily blocking a target nerve to assess if a resulting physiologic response is representative of a desired clinical effect of the procedure.

Confirmation of efficacy may be assessed manually by a practitioner by observing the parameter measurements in real time. Alternatively, confirmation may be assessed automatically by the computerized system console that takes input from the physiologic monitoring equipment and compares it to a stimulation signal profile. Confirmation may also be performed by the software embedded in the IPG. Automatic changes to the block parameters (e.g. current intensity) can be made by software based on the results. Confirmation may include stimulation of the nerve proximate to the block and measurement of nerve activity distal to the block. Recording of nerve signals from nerve cuff electrodes is known.

Confirmation of blocking therapy effectiveness may be accomplished using nerve cuff designs shown in FIGS. 12A and 12B. One exemplary embodiment is illustrated in FIG. 12A. A nerve 190 (e.g., GSN) positioned inside a cuff 191 having four active electrodes is shown. The electrodes are embedded (or affixed) to an insulating material 192 (elastomeric cuff). The electrodes are numbered 1, 2, 3, and 4. This configuration provides a means to deliver electrical nerve blocking therapy and tests the effectiveness of the nerve block by recording stimulation-induced extracellular action potentials post-block. Electrodes 2, 3, and 4 may be used to deliver blocking therapy. An example of inter-electrode distance, d, between the electrodes to provide blocking therapy is 1 to 2 mm. The effects of the electrical blocking therapy is expected to last seconds to minutes after the blocking signal ends. During the post-block period, electrodes 2, 3 and 4 may be used to record extracellular action potentials generated by the proximal electrode 1 in a tri-polar recording configuration that promotes cancelation of common noise. Electrodes 2, 3, and 4 may be switched from delivering a high frequency block to recording extracellular potentials using embedded electronics such as an embodiment of an electrode configuration switch shown in FIG. 16. The DAQ and signal conditioning circuitry (FIG. 16) may provide for acquisition of the extracellular potential as well as filtering and amplification needed for recording. The stimulation via proximal electrode 1 is unipolar with the return electrode in a remote location (e.g., the IPG case). The electrodes may be connected to the IPG using wired connections (see wire 193). The connections provide communication between the nerve 190 and IPG for delivery of HFBS, recording, and nerve stimulation.

In another exemplary embodiment, a nerve cuff 195 has 5 active electrodes (FIG. 12B). In this example, the high frequency block therapy is delivered via electrodes 3, 4, and 5 in a tripolar configuration with electrode 4 acting as a cathode. During the post-block period, electrodes 3, 4, and 5 are used to record the stimulation-induced extracellular action potential. The proximal stimulus may be delivered via proximal electrodes 1 and 2 where the stimulus is bipolar. An example of the inter-electrode distance, d, between the bipolar stimulation electrodes is 2 to 3 mm.

To facilitate a clinically effective procedure, an embodiment may involve confirming that a patient will experience the desired physiologic effect of blocking before final implantation. This may be achieved by electrically blocking the nerve temporarily and observing a physiologic response (e.g., hemodynamic effect). If potential clinical success is assessed to have a physiologic response as desired then permanent implantation may proceed. Conversely, if the physiologic response to temporary blocking is not as desired a physician may decide to not proceed with implantation. Another option is to access the contralateral GSN and evaluate the clinically efficacy.

Figure 13:
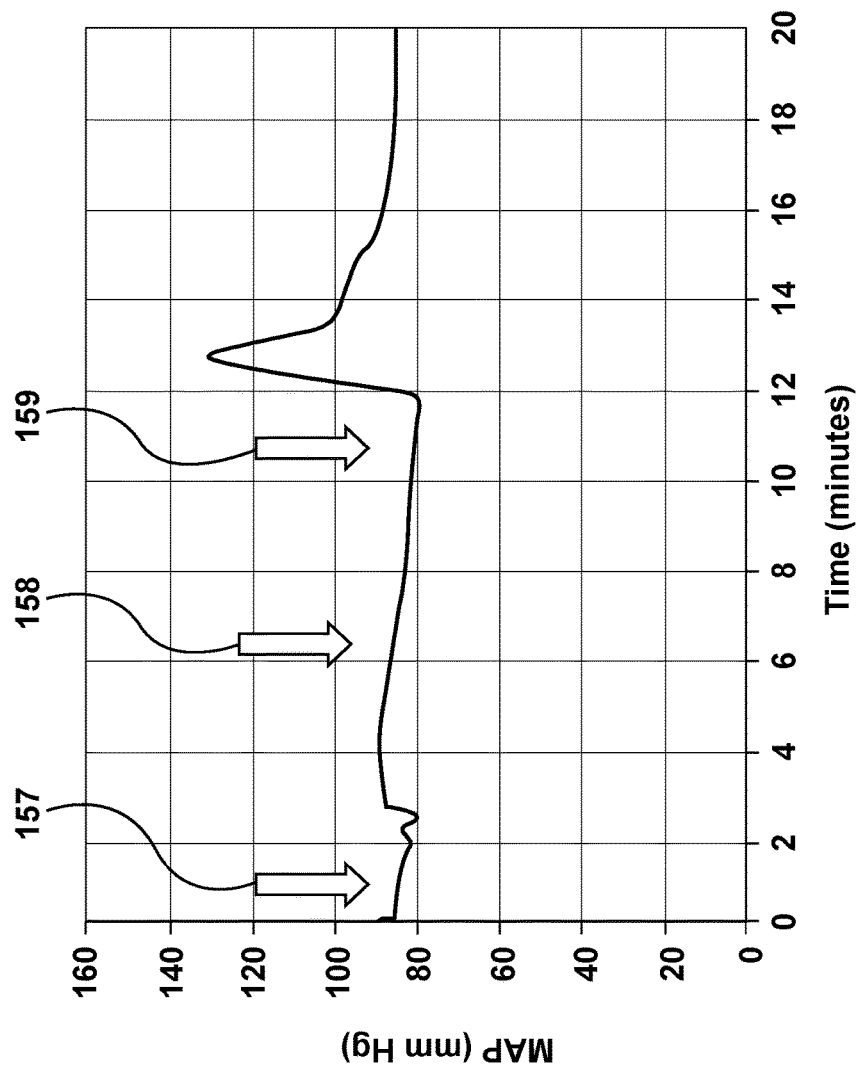
FIG. 13 is a plot of mean arterial pressure over time showing response to stimulation of a blocked nerve.

To confirm this notion FIG. 13 illustrates an experiment where the hemodynamic response to a greater splanchnic nerve stimulation and block with locally injected lidocaine, a nerve blocking agent, was tested in an animal. Time on the X-axis is in minutes. The Y-axis represents mean arterial blood pressure in mmHg. The first arrow 157 from the left indicates the time of injection of lidocaine. The second arrow 158 indicates the time of application of electrical stimulation to the greater splanchnic nerve proximal to the blocked area of the nerve. The term "proximal" as used herein with reference to a relative position on a nerve denotes a location nearer to a point of origin, such as brain, spinal cord, sympathetic chain or a midline of the body and where the term "distal" is used to denote a location further away from the point of origin and closer to the innervated peripheral organ such as splanchnic vascular beds, liver and spleen. Following the first stimulation 158 proximal to the nerve block 157, no or very little physiologic response is observed on arterial blood pressure, or other physiologic parameters that are omitted on this graph for simplicity. The third arrow 159 illustrates electrical stimulation of the greater splanchnic nerve for 30 seconds applied distal to the lidocaine blocked area. The physiologic response manifests by increase of mean arterial blood pressure and other hemodynamic parameters as described in this application.

It is noted that MAP monitoring as mentioned above is an example and hemodynamic monitoring does not necessarily need to be invasive monitoring and may be accomplished with a less invasive monitoring of blood pressure, for example using a Nexfin or ClearSight device (Edwards) for continuous monitoring of hemodynamics commonly used in hospitals. The ClearSight system quickly connects to the patient by wrapping an inflatable cuff around the finger. The ClearSight system provides noninvasive access to automatic, up-to-the-minute hemodynamic information including: SV, CO, SVR, or Continuous Blood Pressure (cBP). Such a monitoring device may be hooked up to a computerized console to communicate physiologic response to the computer, which may determine stimulation or blocking parameters based on the physiologic responses.

Figure 14:
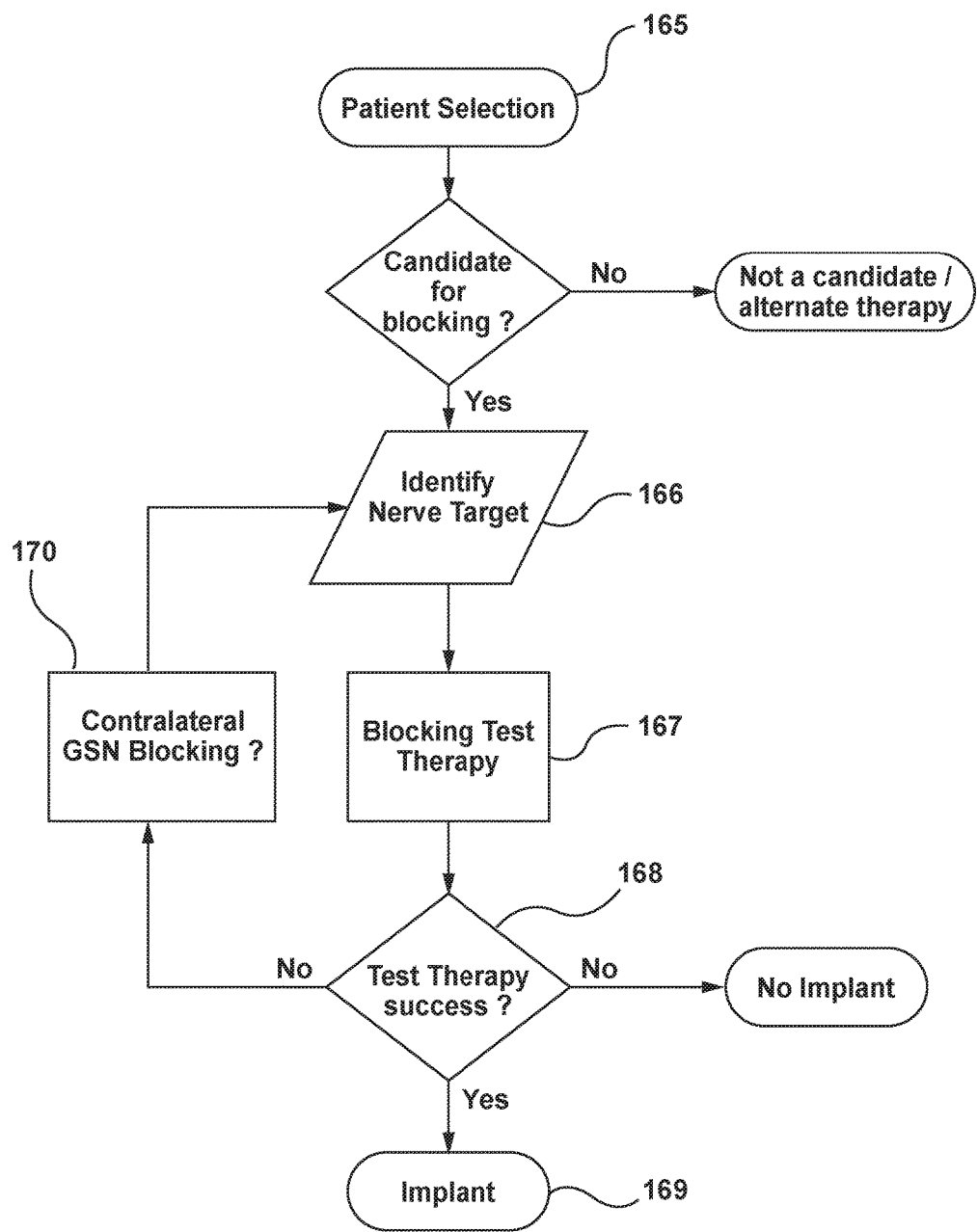
FIG. 14 is a flowchart illustrating the steps from patient selection to permanent implantation.

FIG. 14 is a flowchart that illustrates an example of a process from patient selection to permanent device implantation for blocking of the GSN to treat heart failure. One means for the selection of patients 165 suitable for GSN blocking may include evaluation of splanchnic vascular capacitance. An orthostatic stress test (tilt table test), fluid challenge, exercise test or an appropriate drug challenge can help distinguish low vascular compliance from normal. Orthostatic stress causes blood shifts from the stressed volume to the unstressed volume. In healthy patients, to compensate for the shift, sympathetic tone increases resulting in splanchnic vasoconstriction and rapid mobilization of blood from the unstressed compartment to the active circulation. The hemodynamic response to tilt in chronic CHF is atypical; as there is significantly less peripheral pooling in the upright posture indicating diminished splanchnic vascular capacitance. Acute oral or intravenous fluid challenge is another test to assess splanchnic vascular capacitance. A fluid challenge could test the capacitance by measuring the effects of a fluid bolus on cardiac filling and pulmonary pressures. Patients with low capacitance of the splanchnic venous reservoir will be unable to compensate for the hemodynamic effect of the fluid bolus. Patients with HF, HFPEF and patients with increased SNA will be more likely to respond to the fluid challenge with a disproportional rise in cardiac filing pressure and other related and measurable physiologic parameters. This response could indicate that the patient might be a candidate for GSN ablation therapy. After the patient is identified as a candidate for blocking therapy, the process of identifying the appropriate nerve target 166 is implemented as the first step in the implantation procedure. FIG. 10 illustrates a physiological response to electrical stimulation to identify a target nerve (GSN). After nerve target identification and selection, one means of confirmation of procedural efficacy 167 is to temporarily block the nerve target and evaluate 168 whether the physiological response is consistent with the desired clinical effect. After nerve target identification has been confirmed and procedural efficacy has been confirmed permanent implant 169 be initiated. Confirmation of the technical efficacy or success of the blocking procedure may be accomplished by delivering electrical stimulation proximal to the location of block where a physiological response was elicited prior to electrical block. Absence or attenuation of responses will indicate technical success of the blocking therapy (see FIG. 13). If the blocking therapy is a success, no further action is needed. If the blocking is not successful, the clinician may opt to provide additional blocking 170 therapy at the same site or repeat the procedure of identifying additional nerve targets (e.g., contralateral GSN) and providing blocking therapy as described previously.

Figure 15:
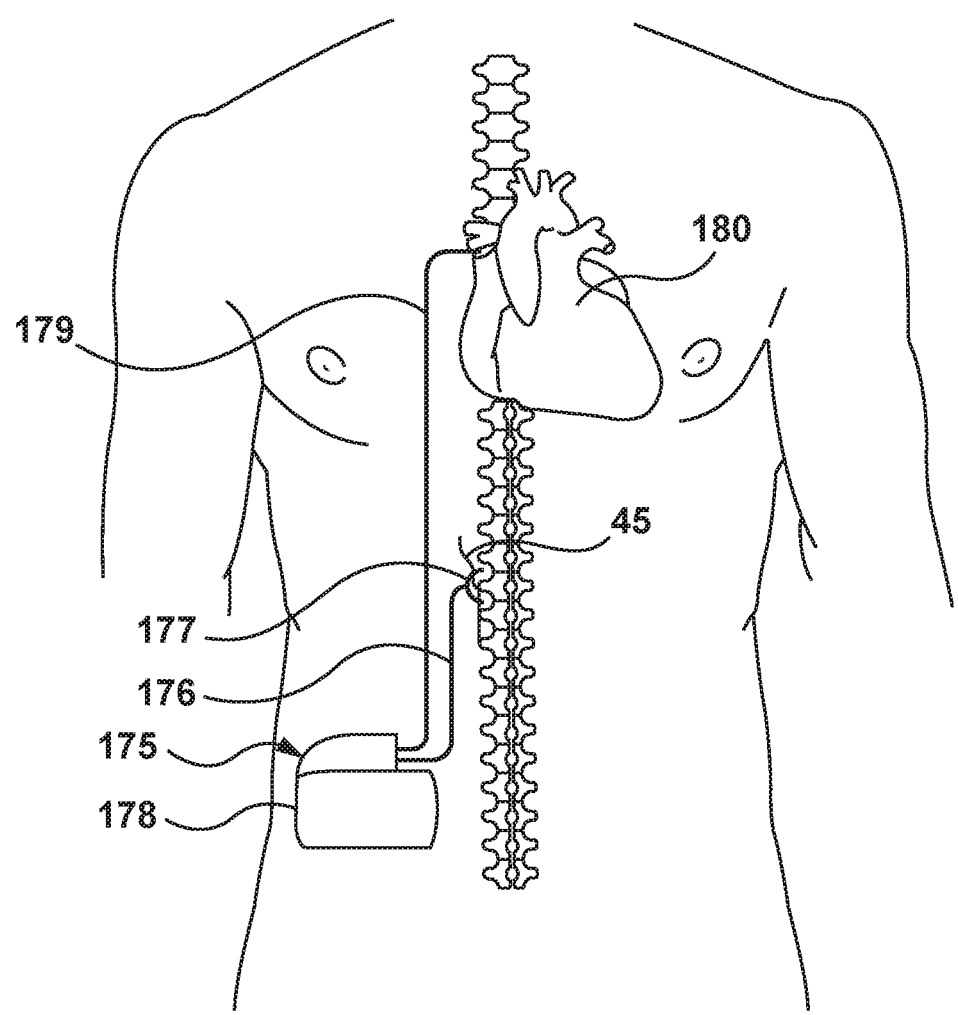
FIG. 15 is a schematic diagram of IPG placement.

In one exemplary embodiment, as illustrated in FIG. 15 a portable and implantable device 175 with lead wires 176 is adapted to terminate at a nerve cuff electrode 177 implanted around a target GSN 45. The lead 176 is tunneled from the nerve cuff 177 implanted around the GSN 45 to the subcutaneous IPG 178 implant site that can be on the patient's abdomen, flank or back. Another lead 179 or leads may be implanted in the heart 180 via the veins of cardiovascular system. The nerves are accessed as described in FIGS. 8, 9, and 11.

The pulse generator 178 for electrical nerve stimulation in an embodiment is implantable and programmable. Programmable pulse generators can employ conventional microprocessors and other standard electrical components. The pulse generators envisioned for use in the present embodiments are able to generate charge balanced, biphasic pulses. The biphasic pulse is repeated continuously to produce the blocking stimulus waveform. The pulse rate will vary depending on the duration of each phase, but will be in the range of 0.5 Hz up to 10 kHz. When the stimulus is delivered at the appropriate rate, typically around 6 kHz, the nerve membrane is rendered incapable of transmitting an action potential. The amplitude of the signal can vary between 0 and 20 mA. This type of conduction block is immediately reversible by ceasing the application of the waveform.

In a further embodiment, it is envisioned that the device and IPG can both receive and transmit signals. For example, it is envisioned that signals could be transmitted from the device to an external programmer or display. Likewise, it is envisioned in a further embodiment that patient or clinician input could be received by the device to modulate the generated pulse, as needed. The pulse generator can be battery operated or operated by a radiofrequency device. Because the IPG, components, and power source of the device may be implanted, it is envisioned that the device is hetinetically sealed.

Figure 16:
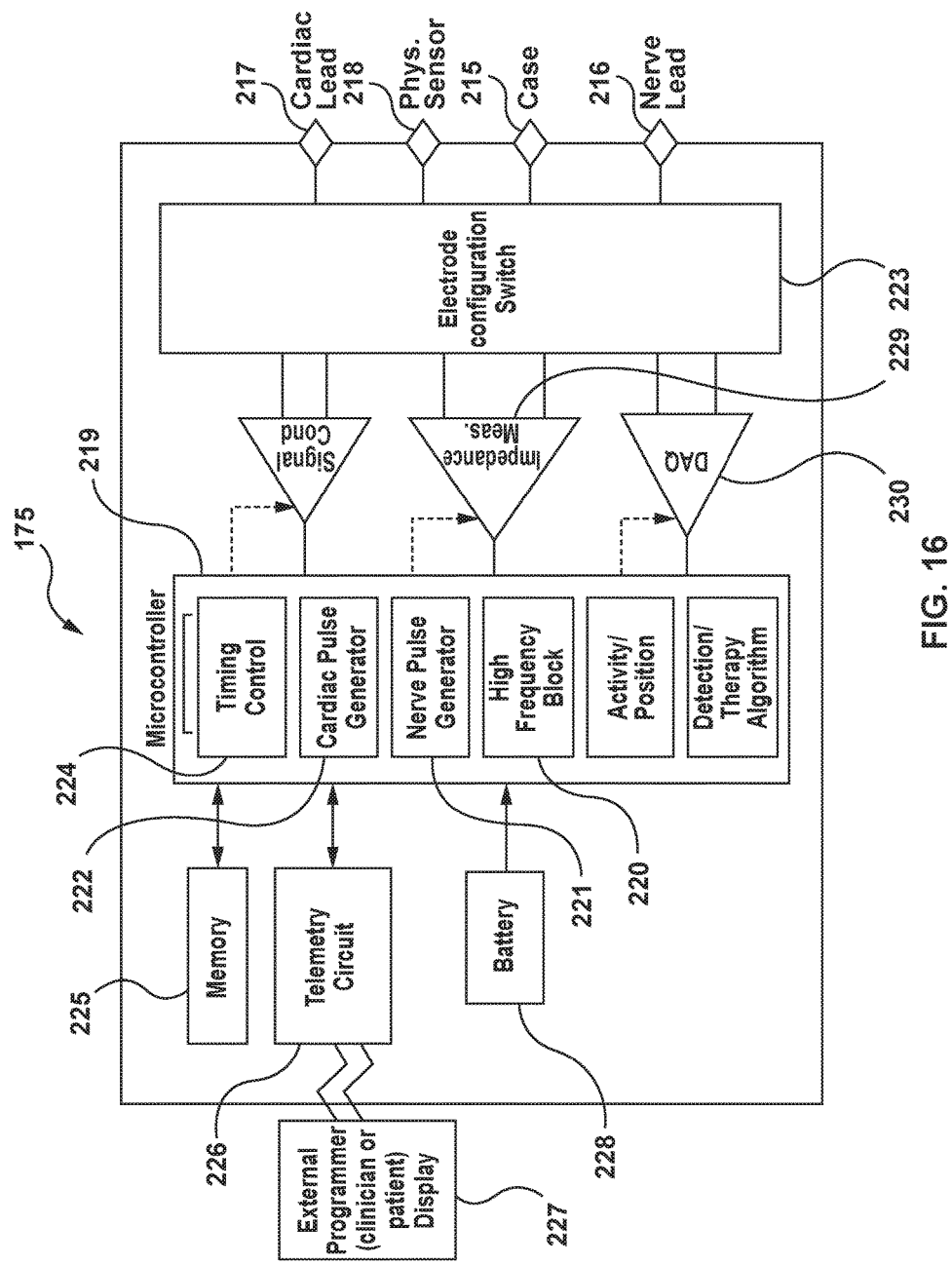
FIG. 16 is a functional block diagram that shows the components and the respective signal flow of components housed in an implantable pulse generator, or stimulus producer, for neuromodulation and cardiac electrical modulation.

A schematic of the implantable pulse generator (IPG) that may be part of a system embodiment is shown in FIG. 16, which also shows various functional components of an implantable device 175. The components are typically contained in a case 215, which can be electrically conductive and connected to the internal electronics of the IPG, which is often referred to as the "can", "housing", "encasing", or "case electrode", and may be programmably selected to act as the return electrode for unipolar operational modes. The case 215 may further be used as a return electrode alone, or in combination with, one or more electrodes for stimulating or blocking purposes. The case may also be used as one of the sensors in determination of lead impedance, for example. The case 215 may be made of a conductive metal, such as titanium, and the implantable device hermetically sealed and leak rate tested.

The case further includes a connector (not shown, e.g., a header or a connector block, made of polyurethane or other suitable material), having a plurality of terminals shown schematically with the names of the leads to which they are connected shown next to the terminals, including: a nerve lead terminal 216, a cardiac lead terminal 217, and a physiological sensor terminal 218 for physiological sensors e.g., a blood pressure probe. The electrical connection from the connector to the circuitry through the hermetically sealed case are typically realized utilizing feedthroughs made of an electrical conductor, such as platinum.

The implantable device 175 may include a programmable microcontroller 219 that controls various operations of the implantable neurostimulator device, including physiological monitoring, nerve blocking therapy, electroneurogram sensing, and cardiac sensing and stimulation therapy. Electroneurogram sensing can be realized using the same cuff electrodes that are used for stimulation and blocking (FIGS. 12A and 12B). The microcontroller includes a microprocessor or equivalent control circuitry, RAM or ROM memory, logic and timing circuitry, state machine circuitry, and I/O circuitry.

The implantable device further includes a high frequency blocking module 220, neurostimulation pulse generator 221, as well as an optional cardiac pulse generator 222 that generate electrical stimulation or blocking pulses for delivery by the neural lead 176 and cardiac lead(s) 179 via an electrode configuration switch. The cardiac function of the device may be atrial or ventricular. The electrode configuration switch 223 may include multiple switches for connecting the desired electrodes to the appropriate I/O circuits, thereby providing complete electrode programmability. Accordingly, the switch, in response to a control signal from the microcontroller 219, determines the polarity of the stimulation pulses (e.g., unipolar, bipolar, etc.) by selectively closing the appropriate combination of switches. The cardiac pulse generator 222 is capable of delivering a single electric pulse that excites myocardium and generates an entire heart muscle contraction (cardiac capture) and the neurostimulation pulse generator 221 is capable of delivering trains of pulses that selectively excite an approximate nerve creating series of action potentials in the nerve fibers. The high frequency blocking 220 is capable of delivering trains of pulses that selectively block the nerve creating temporary blocking of nerve conduction.

The pulse generators and high frequency block module are controlled by the microcontroller via appropriate control signals used to trigger or inhibit the electrical pulses. The microcontroller is illustrated as including timing control circuitry 224 to control the timing of the electrical pulses (e.g., electrical nerve blocking frequency, neural stimulation frequency, cardiac pacing rate, etc.). The timing control circuitry 224 may also be used for the timing of the high frequency block therapy, nerve stimulation periods (duty cycles, pulse widths), cardiac refractory periods, noise detection windows, etc.

In another embodiment, GSN activity may be monitored to control or modulate blocking therapy. GSN activity may be used as a measure of therapy efficacy or as an indication for initiating therapy. Signal conditioning circuits may be selectively coupled to the nerve lead 216 through the switch 223 to detect the presence of greater splanchnic nerve activity. The signal conditioning circuits and may include dedicated sense amplifiers, multiplexed amplifiers, or shared amplifiers. Each sensing circuit may employ one or more low power precision amplifiers with programmable gain or automatic gain control, bandpass filtering, and a threshold detection circuit to selectively sense the nerve signal of interest.

In another embodiment, GSN activity may be monitored to control or modulate blocking therapy. The DAQ module may be used to acquire the electroneurograms. The electroneurograms may be saved to memory and sent to an external system for signal processing. Some processing, such as stimulus artifact reduction, may be performed by the signal conditioning circuit of the IPG. The external system my employ one or more sense amplifiers, multiplexed amplifiers, or shared amplifiers. Each sensing circuit may employ one or more low power precision amplifiers with programmable gain or automatic gain control, bandpass filtering, and a threshold detection circuit to selectively sense the nerve signal of interest. After processing, the telemetry circuit can receive information used to control or modulate blocking therapy.

The operating parameters of the implantable device may be non-invasively programmed into the memory 225 through a telemetry circuit 226 in telemetric communication via a communication link with the external device, such as a clinician programmer or a patient interface 227. In addition to telemetric communication, communication may also be achieved using radio frequency or RF (circuitry not shown). The microcontroller can activate the telemetry circuit with a control signal. The telemetry circuit allows the status information relating to the operation of the device, as contained in the microcontroller 219 or memory 225, to be sent to the external device through the established communication link. The telemetry may be operated on demand by a physician, a care provider who is not a physician, or the patient.

The device additionally includes a battery 228 that provides operating power to all of the components shown in FIG. 16. The battery is capable of operating at low current drains for long periods of time. The battery 228 also desirably has predictable discharge characteristics so that elective replacement time can be detected. The device can further include magnet detection circuitry (not shown), coupled to the microcontroller 219, to detect when a magnet is placed over the device. A magnet may be used by a clinician to perform various test functions of the exemplary device or to signal the microcontroller that a wand of an external programmer is in place to receive or transmit data to the microcontroller through the telemetry circuits. Communication between the device and external devices (clinician programmer, patient interface, sensors, etc.) may also be performed wirelessly using RF communication protocols.

The device further includes an impedance measuring circuit 229 that is enabled by the microcontroller via a control signal. The impedance measuring circuit is used for many purposes, including: lead impedance surveillance during acute and chronic phases for proper lead positioning or dislodgement; detecting operable electrodes and automatically switching to an operable pair if dislodgement occurs; measuring respiration rate, tidal volume or minute ventilation; measuring thoracic impedance; detecting when the device has been implanted; measuring cardiac stroke volume and systolic and diastolic volume of blood in the heart; and so forth. The impedance measuring circuit may be coupled to the switch so that any desired electrode may be used.

In one configuration, the accelerometer output signal from the activity/position sensor is bandpass-filtered, rectified, and integrated at regular timed intervals. A processed accelerometer signal can be used as a raw activity signal. The device derives an activity measurement based on the raw activity signal at intervals timed according to the cardiac cycle or at other suitable time intervals. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state. The activity variance can be monitored during day and night periods set by the telemetry for the geographic area and time zone to detect the low variance in the measurement corresponding to the sleep state.

Figure 17:
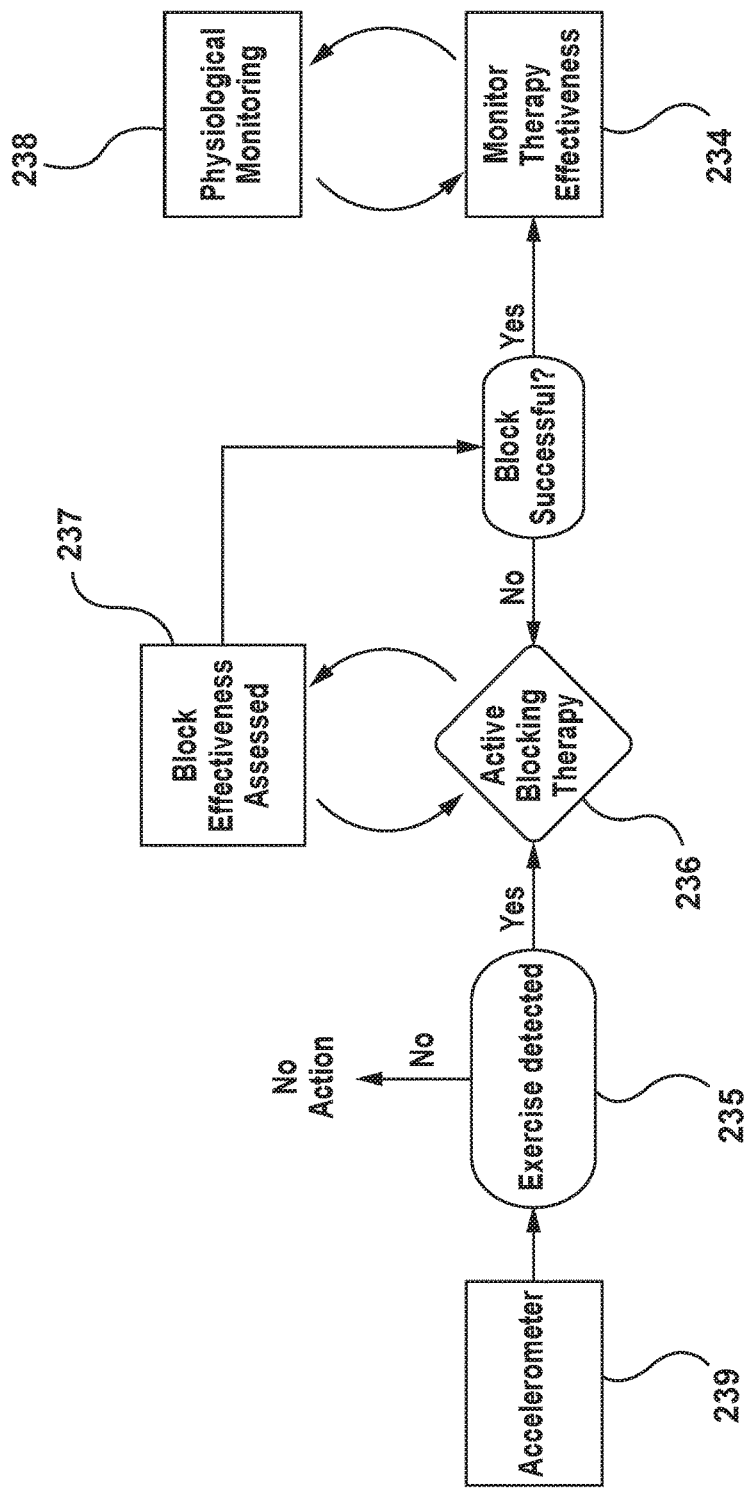
FIG. 17 is a flowchart illustrating the steps for blocking therapy after exercise is detected.

In one embodiment as shown in FIG. 17, the activity signal is used to provide responsive therapy. Patients with HFpEF experience exercise limitations that have a tremendous effect on quality of life. Upon detection of exercise 235, therapy is initiated 236 to increase exercise capacity in these patients. Patients may also initiate therapy prior to exercise. The efficacy of therapy 237 can be derived from the calculation of the activity variance parameter described above. The activity variance is compared over time to indicate exercise time (or exercise capacity) to create a measure of therapy efficacy. Once blocking therapy is initiated 236, the effectiveness of the block may be determined (see FIGS. 12A and 12B). If block is not effective, parameters will be changed until successful blocking is confirmed. Once the blocking is confirmed, physiological sensors will be monitored to determine therapy effectiveness 234. The signal conditioning and DAQ 230 modules in the IPG (FIG. 16) will be used to acquire the physiological signal 238 used to determine therapy effectiveness (Physiological Sensor Module, FIG. 16). High frequency block parameters may be adjusted based on detection from physiological sensors.

Another embodiment of the disclosure uses an accelerometer 239 to monitor position and provide therapy in response to positional conditions. CHF patients may experience fluid back-up in the lungs that results in difficulty breathing at rest or when lying in bed. This results in altered sleep patterns, such as sleeping in an upright position. This significantly reduces sleep quality and results in deterioration of health and quality of life. The accelerometer signal will be used to detect sleeping in upright positions that are indicative of congestion. Detection of altered sleeping patterns will trigger blocking therapy to relieve lung congestion leading to improved sleep quality. The accelerometer signal will be used to detect exercise 235 such as walking or walking up the stairs and activate therapy in HFpEF patients that experience dyspnea from exertion due to elevation of pulmonary blood pressure in response to exercise induced mobilization of splanchnic venous blood into the circulating volume (FIG. 17).

Another embodiment of the disclosure comprises a detection device, a detection algorithm, a treatment device and a treatment algorithm (FIG. 16). The detection and input of a variety of health and heart health indicators (including venous capacitance, unstressed volume, effective circulatory volume, pulmonary pressure, dyspnea, as well as other factors described herein, etc.) is envisioned to help determine the ranges in which the nerve block is initiated, continued or terminated. These inputs, along with the use of additional algorithms are envisioned to help streamline the application of the present therapies. It is important and envisioned that these algorithms are not only accurate and effective for starting, continuing and stopping the generated signal, but also that the system is tolerant of random or isolated stimuli that do not require treatment. Further an algorithm may incorporate information such as a feedback signal, sensor input, or programmable input which may affect its output. In a further embodiment, said device may be configured to receive signals from sensors including fluid or blood pressure (BP) sensor and adjust accordingly to modulate and deliver modified therapy, as needed or desired. Sensors are envisioned to be comprised within the device or separate from the device. Furthermore, it is also envisioned that specifically the leads of the device may also comprises a detector capable of sensing values (e.g., blood pressure, heart rate, cardiac output, acceleration, fluid imbalance, fluid impedance, etc.) and fine tuning delivery of the nerve block to reduce venous congestion.

Figure 18:
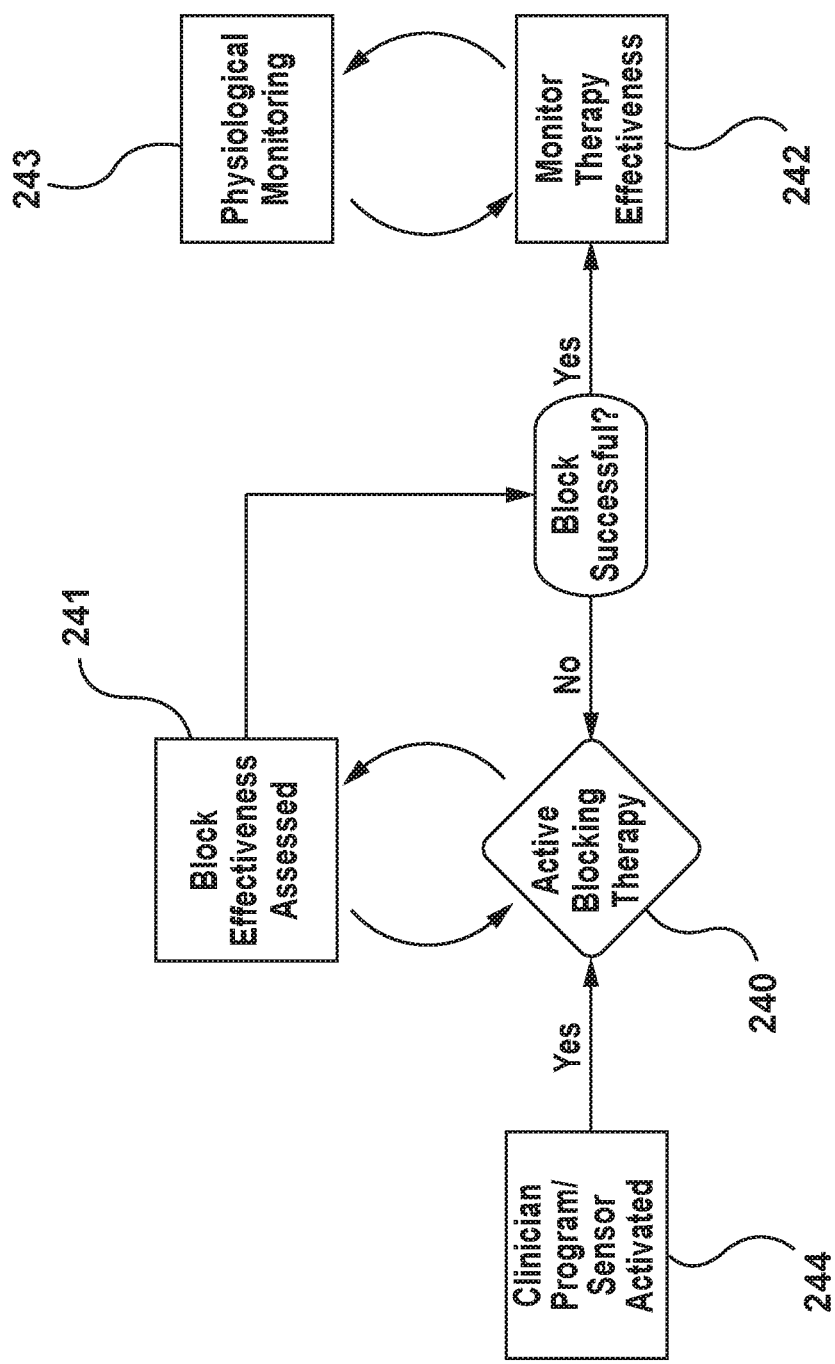
FIG. 18 is a flowchart illustrating the steps for blocking therapy.

While automatic detection followed by the delivery of therapy is envisioned to optimize the ease and convenience and minimize risk of user error during operation, patient-initiated therapy is also envisioned wherein the patient experiences shortness of breath or other symptoms and initiates the therapy 244 for a set amount of time until benefit is achieved. In addition, it is envisioned that the device may be remotely activated and controlled, in coordination or independent of any sensors/algorithms, in such a way that a user, emergency medical personnel or medical practitioner could perform a manual override and operation as required. One embodiment of operation of an implantable system provides for blocking therapy initiation by a clinician, a patient, programmed treatment algorithm, or via sensor activation based on a detection algorithm (see FIG. 18). After therapy is initiated 240, blocking effectiveness is assessed 241. If blocking is not successful, high frequency blocking parameters will be adjusted until blocking is successful. Once blocking success is determined, therapy effectiveness may be assessed 242 by monitoring physiological sensors 243. High frequency blocking parameters may be modified to improve therapy effectiveness. In addition, a programmer or patient programmer can be used to remotely change stimulation parameters as required. For example, maximum allowed stimulation energy may be reduced based on pain sensation by the patient or increased based on medical tests.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

What is claimed is:

1. A method of treating heart failure or symptoms associated with heart failure in a human patient, comprising:
   in a patient with heart failure or symptoms associated with heart failure;
   thoracoscopically accessing at least one greater splanchnic nerve; and
   affixing an implantable neuromodulation device with a tripolar nerve cuff to the at least one greater splanchnic nerve, the tripolar nerve cuff including first, second and third electrodes axially spaced from at least one of the other electrodes, and the axial spacing between adjacent electrodes is 1 to 2 mm the implantable neuromodulation device further comprising a pulse generator, a detection member for detecting at least one physiological parameter, and at least one lead for delivering stimulus to the at least one greater splanchnic nerve through the tripolar nerve cuff,
   wherein the delivered stimulus has a frequency of at least 6 kHz and an amplitude of at least 10 mA to cause a reversible blockage to conduction along the at least one greater splanchnic nerve.

2. The method of claim 1, wherein the at least one greater splanchnic nerve is at least one of a left greater splanchnic nerve and a right greater splanchnic nerve.

3. The method of claim 1, wherein thoracoscopically accessing is selected from the group consisting of transthoracic, transabdominal, percutaneous, access or any combination thereof.

4. The method of claim 1, wherein the patient has diastolic heart failure or symptoms associated with diastolic heart failure.

5. The method of claim 1, wherein said implantable neuromodulation device further comprises a cardiac pulse generator configured to generate electrical stimulation pulses for delivery by one or more cardiac leads.

6. The method of claim 1, wherein the implantable neuromodulation device further comprises a programmable microcontroller configured to control at least one operation of the implantable neuromodulation device.

7. The method of claim 6, wherein the programmable microcontroller controls at least one operation chosen from the group consisting of logic processing, application of nerve blocking therapy, physiological monitoring, electroneurogram sensing, cardiac sensing, and any combination thereof.

8. The method of claim 7, wherein the method of treatment further comprises an exercise detection step whereby the application of nerve blocking therapy may be arrested by the detection of exercise.

9. The method of claim 1, wherein the detection member for detecting at least one physiological parameter is configured to detect a physiological parameter selected from the group consisting of orientation, acceleration, cardiac preload, cardiac afterload, cardiac output, stroke volume, blood pressure, venous congestion, pulmonary congestion, sense of dyspnea, heartrate, end-diastolic volume, end-systolic volume, venous return or any combination thereof.

10. The method of claim 9, further comprising monitoring the physiological parameters to determine a therapy effectiveness.

11. The method of claim 9, further comprising selecting at least one physiological parameter to be transmitted from the implantable neuromodulation device to an external programmer or display.

12. The method of claim 1, further comprising deflating the lung proximate to the at least one greater splanchnic nerve.

* * * * *